(12) United States Patent
MacLean

(10) Patent No.: US 9,107,659 B2
(45) Date of Patent: *Aug. 18, 2015

(54) SNAP FIT SLING ANCHOR SYSTEM AND RELATED METHODS

(75) Inventor: Brian MacLean, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 192 days.

This patent is subject to a terminal disclaimer.

(21) Appl. No.: 13/242,821

(22) Filed: Sep. 23, 2011

(65) Prior Publication Data

US 2012/0010462 A1    Jan. 12, 2012

Related U.S. Application Data

(63) Continuation of application No. 11/180,167, filed on Jul. 13, 2005, now Pat. No. 8,043,205.

(51) Int. Cl.
| | | |
|---|---|---|
| *A61F 2/00* | (2006.01) | |
| *A61B 17/06* | (2006.01) | |
| *A61F 2/08* | (2006.01) | |
| *A61B 17/00* | (2006.01) | |

(52) U.S. Cl.
CPC ..... *A61B 17/06109* (2013.01); *A61B 17/06066* (2013.01); *A61F 2/0045* (2013.01); *A61B 2017/0046* (2013.01); *A61B 2017/00805* (2013.01); *A61B 2017/06009* (2013.01); *A61B 2017/06076* (2013.01); *A61F 2002/0823* (2013.01); *A61F 2220/0008* (2013.01)

(58) Field of Classification Search
CPC .......... A61B 17/0401; A61B 17/064–17/0644; A61B 17/844; A61B 2017/0401–2017/0408; A61B 2017/0464; A61F 2/0811; A61F 2002/0817; A61F 2002/0823; A61F 2002/0829; A61F 2002/0835; A61F 2002/0841
USPC ........................ 600/29–31, 37; 606/139–158; 623/23.64–23.71
See application file for complete search history.

(56) References Cited

U.S. PATENT DOCUMENTS

| | | |
|---|---|---|
| 3,003,155 A | 10/1961 | Mielzynski et al. |
| 5,013,136 A | 5/1991 | Whitehead et al. |
| 5,112,344 A | 5/1992 | Petros |
| 5,197,983 A | 3/1993 | Berman et al. |
| 5,250,054 A | 10/1993 | Li |
| 5,425,740 A | 6/1995 | Hutchinson, Jr. |
| 5,439,470 A | 8/1995 | Li |
| 5,439,474 A | 8/1995 | Li |

(Continued)

FOREIGN PATENT DOCUMENTS

| | | |
|---|---|---|
| AU | 4092199 A | 12/1999 |
| CA | 2333121 A1 | 11/1999 |

(Continued)

OTHER PUBLICATIONS

"New Improvements in the Treatment of Female Stress Incontinence", European Association of Urologists, American Medical Systems, 2003.

(Continued)

*Primary Examiner* — Catherine B Kuhlman

(57) ABSTRACT

The invention provides, in various embodiments, systems, devices and methods relating to employing soft tissue anchors in combination with an implantable sling to treat urinary incontinence.

17 Claims, 13 Drawing Sheets

(56) References Cited

U.S. PATENT DOCUMENTS

| | | |
|---|---|---|
| 5,443,472 A | 8/1995 | Li |
| 5,449,366 A | 9/1995 | Li |
| 5,464,189 A | 11/1995 | Li |
| 5,500,000 A | 3/1996 | Feagin et al. |
| 5,520,703 A | 5/1996 | Essig et al. |
| 5,549,636 A | 8/1996 | Li |
| 5,575,805 A | 11/1996 | Li |
| 5,611,515 A | 3/1997 | Benderev et al. |
| 5,643,266 A | 7/1997 | Li |
| 5,645,589 A | 7/1997 | Li |
| 5,649,937 A | 7/1997 | Bito et al. |
| 5,690,649 A | 11/1997 | Li |
| 5,697,931 A | 12/1997 | Thompson |
| 5,702,215 A | 12/1997 | Li |
| 5,707,395 A | 1/1998 | Li |
| 5,715,942 A | 2/1998 | Li et al. |
| 5,741,300 A | 4/1998 | Li |
| 5,776,147 A | 7/1998 | Dolendo |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,922,026 A | 7/1999 | Chin |
| 5,935,138 A | 8/1999 | McJames, II et al. |
| 5,954,057 A | 9/1999 | Li |
| 6,022,373 A | 2/2000 | Li |
| 6,039,686 A | 3/2000 | Kovac |
| 6,039,761 A | 3/2000 | Li et al. |
| 6,042,534 A | 3/2000 | Gellman et al. |
| 6,042,582 A | 3/2000 | Ray |
| 6,096,060 A | 8/2000 | Fitts et al. |
| 6,099,538 A | 8/2000 | Moses et al. |
| 6,110,101 A | 8/2000 | Tihon et al. |
| 6,117,161 A | 9/2000 | Li et al. |
| 6,129,762 A | 10/2000 | Li |
| 6,149,669 A | 11/2000 | Li |
| 6,200,330 B1 | 3/2001 | Benderev et al. |
| 6,224,616 B1 | 5/2001 | Kugel |
| 6,273,852 B1 | 8/2001 | Lehe et al. |
| 6,355,053 B1 | 3/2002 | Li |
| 6,406,423 B1 | 6/2002 | Scetbon |
| 6,451,030 B2 | 9/2002 | Li et al. |
| 6,452,450 B1 | 9/2002 | Enriquez |
| 6,464,706 B1 * | 10/2002 | Winters ............. 623/13.14 |
| 6,478,727 B2 | 11/2002 | Scetbon |
| 6,491,703 B1 | 12/2002 | Ulmsten |
| 6,506,190 B1 | 1/2003 | Walshe |
| 6,530,943 B1 | 3/2003 | Hoepffner et al. |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,685,629 B2 | 2/2004 | Therin |
| 6,691,711 B2 | 2/2004 | Raz et al. |
| 6,695,855 B1 | 2/2004 | Gaston |
| 6,786,861 B1 | 9/2004 | Pretorius |
| 6,808,486 B1 | 10/2004 | O'Donnell |
| 6,808,487 B2 | 10/2004 | Migliari |
| 6,852,330 B2 | 2/2005 | Bowman et al. |
| 6,884,212 B2 | 4/2005 | Thierfelder et al. |
| 6,884,428 B2 | 4/2005 | Binette et al. |
| 6,911,003 B2 | 6/2005 | Anderson et al. |
| 6,936,052 B2 | 8/2005 | Gellman et al. |
| 6,960,160 B2 | 11/2005 | Browning |
| 6,971,252 B2 | 12/2005 | Therin et al. |
| 6,986,780 B2 | 1/2006 | Rudnick et al. |
| 7,025,063 B2 | 4/2006 | Snitkin et al. |
| 7,070,556 B2 | 7/2006 | Anderson et al. |
| 7,083,568 B2 | 8/2006 | Neisz et al. |
| 7,083,637 B1 | 8/2006 | Tannhauser |
| 7,121,997 B2 | 10/2006 | Kammerer et al. |
| 7,131,944 B2 | 11/2006 | Jacquetin |
| 7,361,138 B2 | 4/2008 | Wagner et al. |
| 7,527,588 B2 | 5/2009 | Zaddem et al. |
| 7,878,969 B2 | 2/2011 | Chu et al. |
| 8,043,205 B2 * | 10/2011 | MacLean .................. 600/37 |
| 2001/0049467 A1 | 12/2001 | Lehe et al. |
| 2002/0078964 A1 | 6/2002 | Kovac et al. |
| 2002/0082619 A1 * | 6/2002 | Cabak et al. ............ 606/151 |
| 2002/0083820 A1 | 7/2002 | Greenhalgh |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0133236 A1 | 9/2002 | Rousseau |
| 2002/0138025 A1 | 9/2002 | Gellman et al. |
| 2002/0147382 A1 | 10/2002 | Neisz et al. |
| 2002/0156476 A1 * | 10/2002 | Wilford ..................... 606/72 |
| 2002/0156487 A1 | 10/2002 | Gellman et al. |
| 2002/0161382 A1 * | 10/2002 | Neisz et al. ............. 606/151 |
| 2002/0183762 A1 | 12/2002 | Anderson et al. |
| 2002/0188169 A1 | 12/2002 | Kammerer et al. |
| 2003/0004399 A1 | 1/2003 | Belson |
| 2003/0004580 A1 | 1/2003 | Sump et al. |
| 2003/0004581 A1 | 1/2003 | Rousseau |
| 2003/0065246 A1 | 4/2003 | Inman et al. |
| 2003/0075792 A1 | 4/2003 | Ruhland |
| 2003/0078468 A1 | 4/2003 | Skiba et al. |
| 2003/0078604 A1 | 4/2003 | Walshe |
| 2003/0114865 A1 | 6/2003 | Sater |
| 2003/0114866 A1 | 6/2003 | Ulmsten et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 * | 10/2003 | Browning .................. 600/29 |
| 2003/0191480 A1 | 10/2003 | Ulmsten et al. |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0004600 A1 | 1/2004 | Yoneno et al. |
| 2004/0005353 A1 | 1/2004 | Lopez-Berestein et al. |
| 2004/0006353 A1 | 1/2004 | Bosley et al. |
| 2004/0015048 A1 | 1/2004 | Neisz et al. |
| 2004/0015057 A1 | 1/2004 | Rocheleau et al. |
| 2004/0039453 A1 | 2/2004 | Anderson et al. |
| 2004/0039456 A1 | 2/2004 | Davlin et al. |
| 2004/0068159 A1 | 4/2004 | Neisz et al. |
| 2004/0087970 A1 | 5/2004 | Chu et al. |
| 2004/0097974 A1 | 5/2004 | De Leval |
| 2004/0106847 A1 * | 6/2004 | Benderev .................. 600/37 |
| 2004/0133217 A1 | 7/2004 | Watschke |
| 2004/0144395 A1 | 7/2004 | Evans et al. |
| 2004/0230092 A1 | 11/2004 | Thierfelder et al. |
| 2004/0243166 A1 | 12/2004 | Odermatt et al. |
| 2004/0249240 A1 | 12/2004 | Goldmann et al. |
| 2004/0249397 A1 | 12/2004 | Delorme et al. |
| 2004/0249473 A1 | 12/2004 | Delorme et al. |
| 2004/0267088 A1 | 12/2004 | Kammerer |
| 2005/0004424 A1 | 1/2005 | Raz et al. |
| 2005/0004426 A1 | 1/2005 | Raz et al. |
| 2005/0004427 A1 | 1/2005 | Cervigni |
| 2005/0004576 A1 | 1/2005 | Benderev |
| 2005/0021086 A1 | 1/2005 | De Leval |
| 2005/0043820 A1 | 2/2005 | Browning |
| 2005/0055027 A1 | 3/2005 | Yeung et al. |
| 2005/0065395 A1 | 3/2005 | Mellier |
| 2005/0070829 A1 | 3/2005 | Therin et al. |
| 2005/0080317 A1 | 4/2005 | Merade |
| 2005/0107805 A1 * | 5/2005 | Bouffier et al. ............ 606/119 |
| 2005/0107834 A1 | 5/2005 | Freeman et al. |
| 2005/0234460 A1 * | 10/2005 | Miller ...................... 606/72 |
| 2005/0245787 A1 | 11/2005 | Cox et al. |
| 2005/0250977 A1 | 11/2005 | Montpetit et al. |
| 2005/0261547 A1 | 11/2005 | Bouffier |
| 2005/0267325 A1 | 12/2005 | Bouchier et al. |
| 2005/0278037 A1 | 12/2005 | Delorme et al. |

(56) References Cited

U.S. PATENT DOCUMENTS

| | | |
|---|---|---|
| 2006/0041185 A1 | 2/2006 | Browning |
| 2006/0058575 A1 | 3/2006 | Zadem |
| 2006/0058578 A1 | 3/2006 | Browning |
| 2006/0089525 A1 | 4/2006 | Mamo et al. |
| 2006/0205995 A1 | 9/2006 | Browning |
| 2007/0015953 A1 | 1/2007 | Maclean |
| 2007/0021649 A1 | 1/2007 | Nowlin et al. |
| 2007/0055095 A1 | 3/2007 | Chu et al. |
| 2008/0081945 A1 | 4/2008 | Toso et al. |
| 2010/0197999 A1 | 8/2010 | Deegan et al. |
| 2010/0198003 A1 | 8/2010 | Morningstar et al. |
| 2010/0261955 A1 | 10/2010 | O'Hern et al. |
| 2011/0098526 A1 | 4/2011 | Chu et al. |
| 2011/0288368 A1 | 11/2011 | VanDeWeghe et al. |
| 2011/0319704 A1 | 12/2011 | Chu |
| 2012/0289770 A1 | 11/2012 | Chu |
| 2012/0289980 A1 | 11/2012 | Ostrovsky et al. |

FOREIGN PATENT DOCUMENTS

| | | | |
|---|---|---|---|
| CA | 2427882 A1 | 4/2002 | |
| EP | 0632999 A1 | 1/1995 | |
| EP | 0643945 A2 | 3/1995 | |
| EP | 0677297 B1 | 12/2000 | |
| EP | 1191902 A1 | 4/2002 | |
| EP | 0774240 B1 | 3/2003 | |
| EP | 1342454 A1 | 9/2003 | |
| EP | 1345550 A2 | 9/2003 | |
| EP | 1333776 B1 | 6/2004 | |
| EP | 1324705 B1 | 8/2006 | |
| EP | 1079740 B1 | 8/2007 | |
| FR | 2811218 A1 | 1/2002 | |
| FR | 2852818 A1 | 10/2004 | |
| GB | 2382993 A | 6/2003 | |
| WO | 95/18571 A1 | 7/1995 | |
| WO | 97/13465 A1 | 4/1997 | |
| WO | 97/16121 A1 | 5/1997 | |
| WO | 98/35632 A1 | 8/1998 | |
| WO | 99/59477 A1 | 11/1999 | |
| WO | 00/40158 A2 | 7/2000 | |
| WO | 00/74594 A1 | 12/2000 | |
| WO | 00/74613 A1 | 12/2000 | |
| WO | 01/06951 A1 | 2/2001 | |
| WO | 01/45588 A2 | 6/2001 | |
| WO | 01/78609 A2 | 10/2001 | |
| WO | 02/02031 A1 | 1/2002 | |
| WO | 02/19945 A2 | 3/2002 | |
| WO | 02/26108 A2 | 4/2002 | |
| WO | 02/28312 A1 | 4/2002 | |
| WO | 02/30293 A1 | 4/2002 | |
| WO | 0232284 A2 | 4/2002 | |
| WO | 02/39890 A2 | 5/2002 | |
| WO | 02/069781 A2 | 9/2002 | |
| WO | 02/071953 A2 | 9/2002 | |
| WO | 02/078548 A1 | 10/2002 | |
| WO | 02/078568 A1 | 10/2002 | |
| WO | 03/002027 A1 | 1/2003 | |
| WO | 03/002029 A1 | 1/2003 | |
| WO | 03/007847 A1 | 1/2003 | |
| WO | 03/028584 A2 | 4/2003 | |
| WO | 03/032867 A1 | 4/2003 | |
| WO | WO 03034939 A1 * | 5/2003 | ............... A61F 2/00 |
| WO | 03/071962 A2 | 9/2003 | |
| WO | 03/073960 A1 | 9/2003 | |
| WO | 03/075792 A1 | 9/2003 | |
| WO | WO 03071962 A2 * | 9/2003 | ............. A61B 17/68 |
| WO | 03/086205 A2 | 10/2003 | |
| WO | 03/096928 A1 | 11/2003 | |
| WO | 03/096929 A1 | 11/2003 | |
| WO | 03/096930 A1 | 11/2003 | |
| WO | 2004/004600 A1 | 1/2004 | |
| WO | 2004/012626 A1 | 2/2004 | |
| WO | 2004/016196 A2 | 2/2004 | |
| WO | 2004012579 A2 | 2/2004 | |
| WO | 2004/019786 A1 | 3/2004 | |
| WO | 2004/045457 A1 | 6/2004 | |
| WO | 2005/007079 A2 | 1/2005 | |
| WO | 2005/094721 A1 | 10/2005 | |
| WO | 2005/112842 A1 | 12/2005 | |
| WO | 2005/122721 A2 | 12/2005 | |
| WO | 2005/122954 A1 | 12/2005 | |
| WO | 2009102945 A2 | 8/2009 | |
| WO | 2012154742 A1 | 11/2012 | |

OTHER PUBLICATIONS

Kovac, et al., "Pubic Bone Suburethral Stabilization Sling for Recurrent Urinary Incontinence", Obstetrics & Gynecology, vol. 89, No. 4, Apr. 1997, pp. 493-642. Web page available at: http://journals.lww.com/greenjournal/Abstract/1997/04000/Pubic_Bone.

Palma et al., "A Readjustable Minimally Invasive Sling for Female Urinary Stress Incontinence", SafyrenTM, International Journal of the Brazilian Society of Urology, vol. 29 No. 4, 2003, pp. 353-359.

Siegel, A. L., "Vaginal Mesh Extrusion Associated with use of Mentor Transobturator Sling", Elsevier, Inc., Adult Urology, 2005, pp. 995-999.

Dargent et al., "Insertion of a sub urethral sling through the obturating membrane in the treatment of female urinary incontinence", Gynécol Obstét Fertil, vol. 30, 2002, pp. 576-582.

Dargent et al., "Pose d'un ruban sous uretral oblique par voie obturatrice dans le traitement de l'incontinence urinaire feminine", Gynécol Obstét Fertil, vol. 30, 2002, pp. 576-582.

De Leval, J., "Novel Surgical Technique for the Treatment of Female Stress Urinary Incontinence: Transobturator Vaginal Tape Inside-Out", European Urology vol. 44, 2003, pp. 724-730.

Delorme et al., "Transobturator Tape (Uratape®): A New Minimally-Invasive Procedure to Treat Female Urinary Incontinence", European Urology 45, 2004, pp. 203-207.

Delorme, E., "The transobdurator band: a minimmaly invasive procedure for treatment of urinary stress incontinence in women", Progress in Urology, vol. 11, 2001, pp. 1306-1313.

Hermieu et al., "Les bandelettes sous-urétrales synthétiques dans le traitement de l'incontinence urinaire d'effort féminine", Progrés en Urologie, vol. 13, 2003, pp. 636-647.

Ingelman-Sundberg et al., "Surgical Treatment of Female Urinary Stress Incontinence", Contr. Gynec Obstet, vol. 10, 1983, pp. 51-69.

Nickel, R. F., "Transpelvic Sling Urethroplasty with and without Colpususpension for the Treatment of Complicated Urinary Incontinence in Bitches", Third Annual Scientific meeting (ECVS), Riccione, Jun. 23-26, 1994.

Final Office Action for U.S. Appl. No. 13/463,503, mailed Jan. 2, 2014, 14 pages.

Non Final Office Action for U.S. Appl. No. 13/463,501, mailed Apr. 23, 2014, 20 pages.

Non Final Office Action for U.S. Appl. No. 11/180,167, mailed on Jun. 4, 2010, 12 pages.

Non Final Office Action for U.S. Appl. No. 11/180,167, mailed on Nov. 12, 2010, 11 pages.

Non Final Office Action Response for U.S. Appl. No. 11/180,167, filed Jan. 21, 2011, 8 pages.

Final Office Action for U.S. Appl. No. 11/180,167, mailed on Mar. 28, 2011, 11 pages.

Notice of Allowance for U.S. Appl. No. 11/180,167, mailed on Jul. 18, 2011, 8 pages.

Non-Final Office Action for U.S. Appl. No. 13/463,503, mailed on Aug. 27, 2014, 14 pages.

Office Action for European Patent Application No. 05770753.1, mailed on Apr. 16, 2013, 5 pages.

Office Action response for European Patent Application No. 05770753.1, filed on Aug. 15, 2013, 6 pages.

"The Confident approach to curing incontinence", Monarc Subfascial Hammock, Product Specification, American Medical Systems, Inc., 5 pages.

Final Office Action for U.S. Appl. No. 13/463,501, mailed Dec. 3, 2014, 19 pages.

* cited by examiner

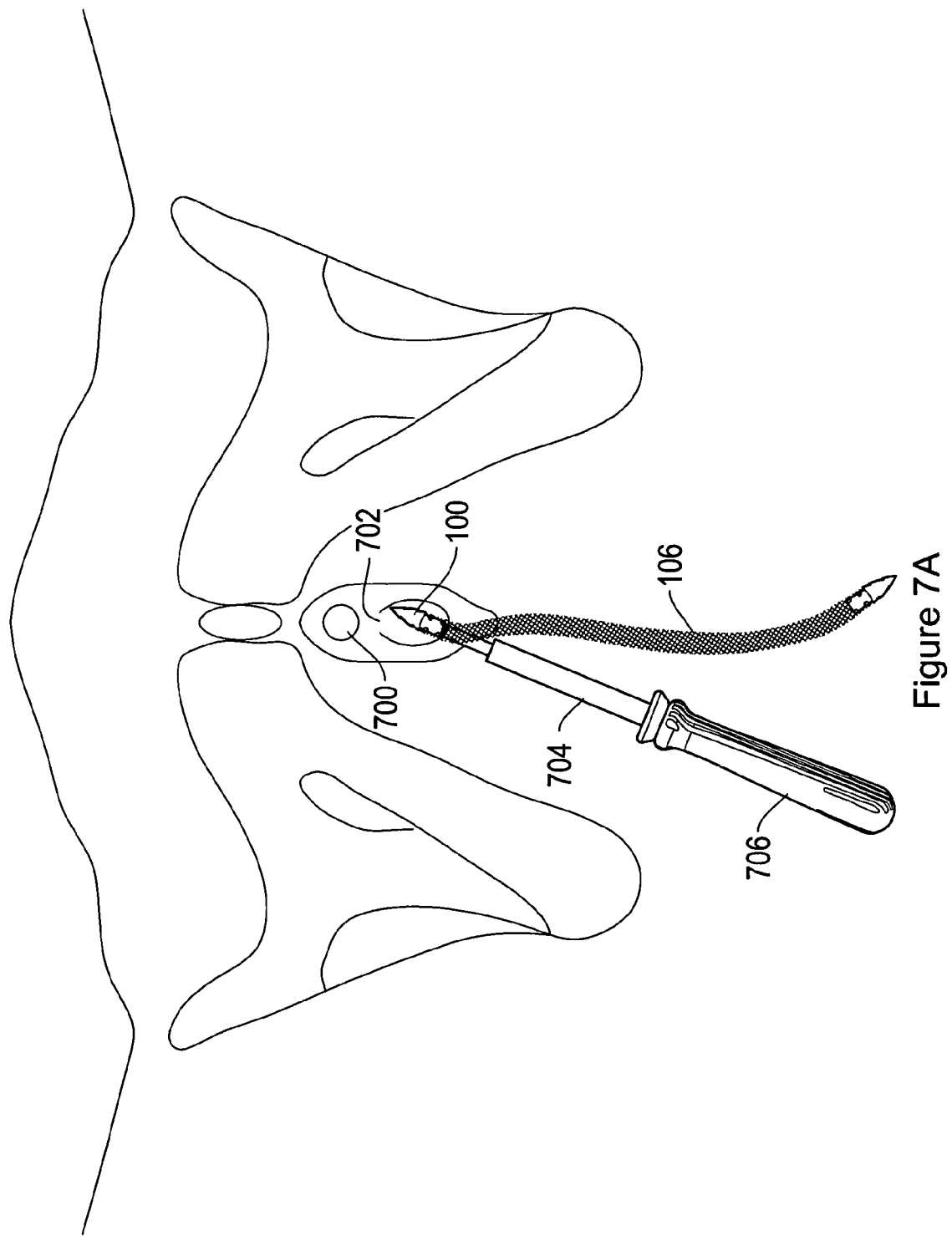

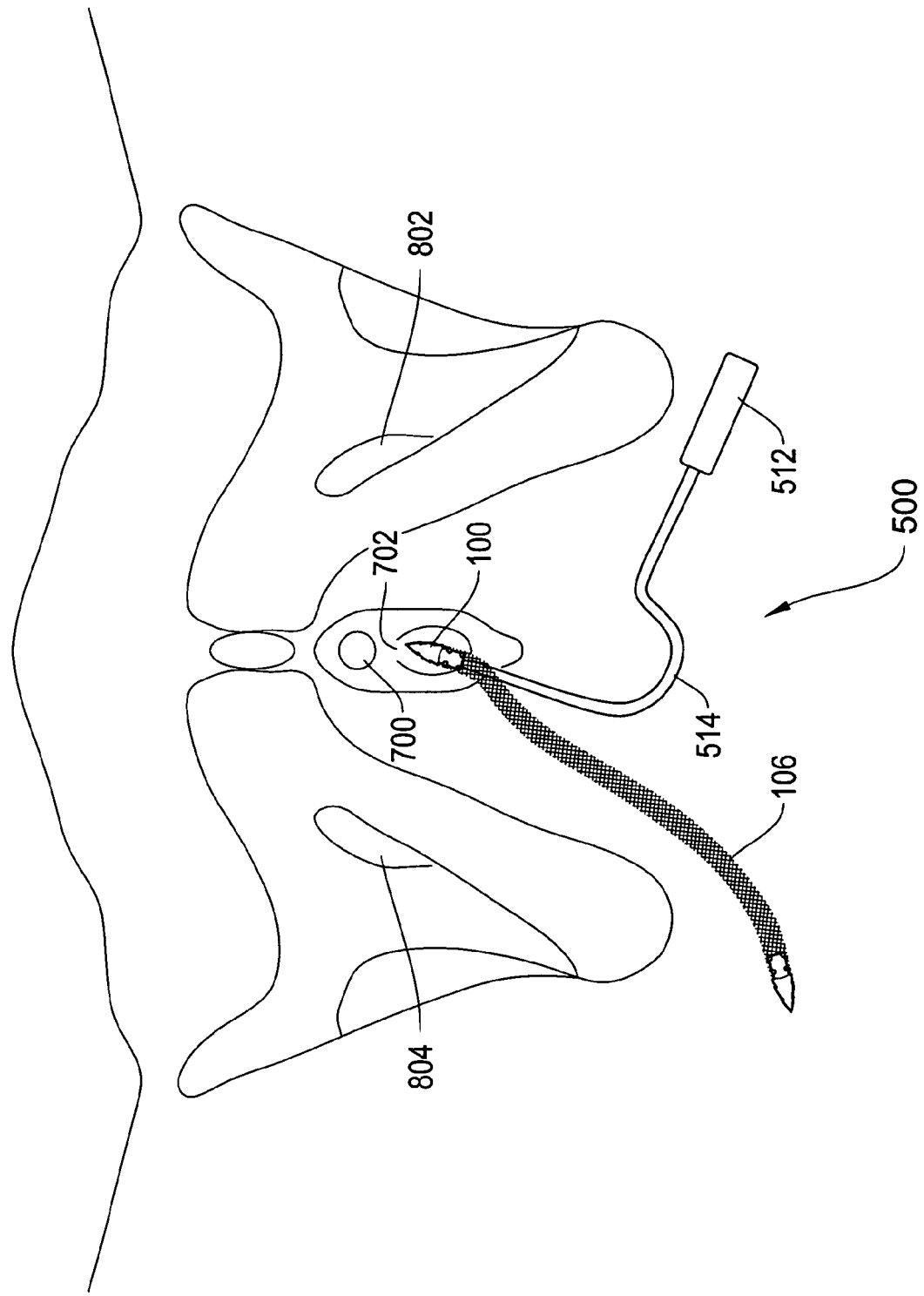

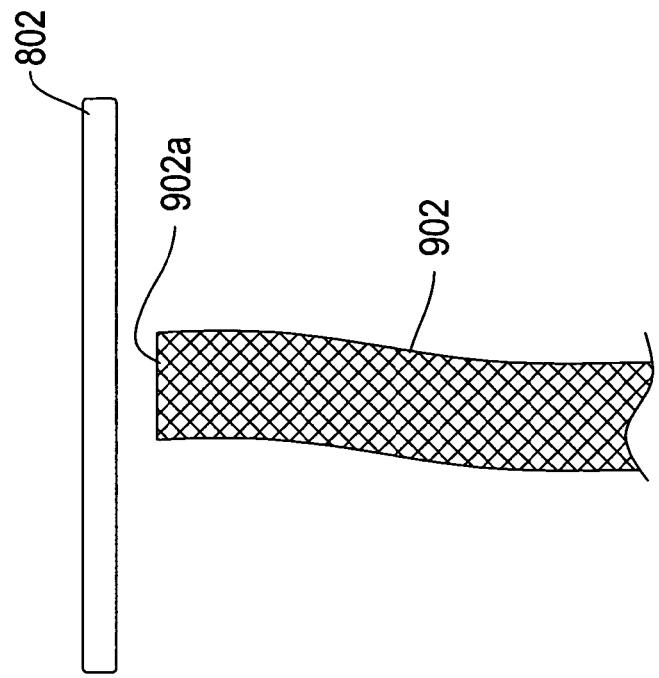
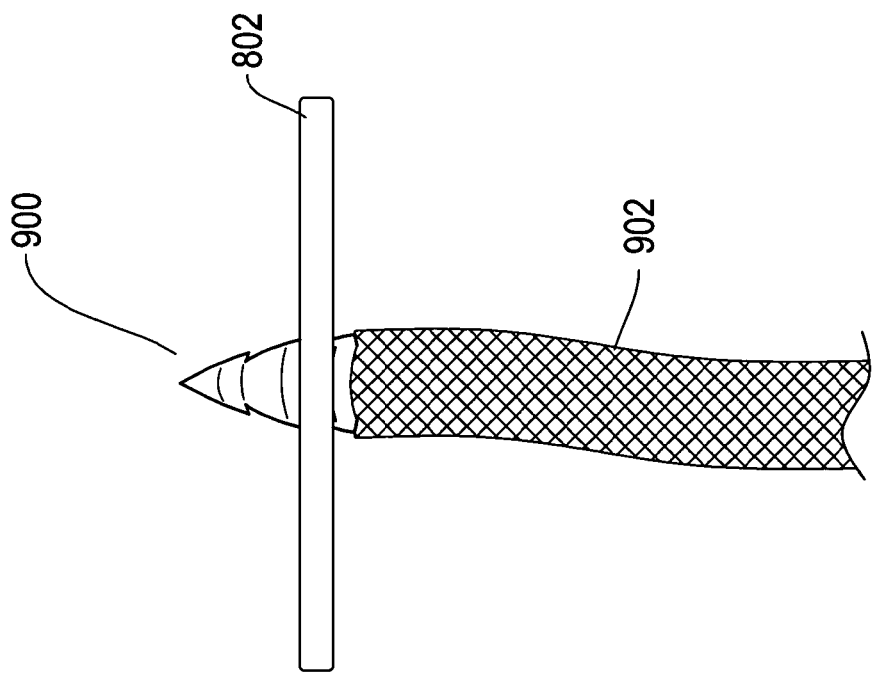

SNAP FIT SLING ANCHOR SYSTEM AND RELATED METHODS

CROSS REFERENCE TO RELATED APPLICATIONS

This application is a continuation of U.S. patent application Ser. No. 11/180,167, filed Jul. 13, 2005, entitled "SNAP FIT ANCHOR SYSTEM AND RELATED METHODS," the disclosure of which is incorporated by reference herein in its entirety.

TECHNICAL FIELD

The invention generally relates to systems and methods for delivering a supportive sling to an anatomical location in a patient. More particularly, in various embodiments, the invention relates to an anchor system for attaching to an end of a sling or sling assembly for affixing the sling in place.

BACKGROUND

Stress urinary incontinence (SUI) affects primarily women, but also men, and is generally caused by two conditions, intrinsic sphincter deficiency (IS D) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow.

A popular treatment of SUI uses a surgical sling placed under the bladder neck or the mid-urethra to provide a urethral platform. Placement of the sling limits the endopelvis fascia drop. The sling is traditionally affixed using a bone anchoring method. Recent advances in surgical techniques have demonstrated the effectiveness of anchorless approaches toward midurethra sling stabilization. However, conventional anchorless techniques suffer from some deficiencies. For example, many do not provide an easily used mechanism for anchoring a sling in place, at least temporarily. Others do not provide an easily used mechanism for adjusting the length of the sling based, for example, on application and patient size.

Accordingly, there is a need for an improved approach to sling placement that simplifies the procedure and reduces trauma to the patient.

SUMMARY

The systems and methods described herein are generally directed to the treatment of stress urinary incontinence. More particularly, in various embodiments, the invention provides systems and methods relating to delivering a supportive sling to the periurethral tissue of a patient, without the need for abdominal or ishiopubic incisions. According to further embodiments, the invention makes it easier for a medical operator to accurately place the supportive sling at a desired anatomical location. In other embodiments, the invention makes it easier for a medical operator to disassociate a sling from a delivery device and/or a remaining portion of a sling assembly. According to additional embodiments, the invention makes it easier to attach an anchor to an end of the sling and to adjust the length of the sling by varying the placement of the anchor.

In one aspect, the invention provides a tissue anchor including a fixation portion and a body portion. The fixation portion may have any shape suitable for affixing the anchor within an anatomical membrane, muscle, ligament, soft tissue, bone or other anatomical site. By way of example, the fixation portion may have edges, tapers, barbs or other protrusions for anchoring the fixation portion in place. The body portion attaches to the sling. According to one embodiment, the body portion is separable into first and second sections, between which a sling end may be interfitted to attach the sling end to the tissue anchor. In one implementation, the first and second body sections are two separate and distinct parts sized and shaped to fit together. According to another implementation, the first and second body sections are hinged such that they remain connected to each other when separated/opened to introduce a sling end. In either case, the body sections may be interfitted together, for example, by way of snap fitting, heat staking, press fitting, gluing or other suitable mechanism.

According to one configuration, the first body section includes one or more apertures (which, optionally, may be through apertures), and the second body section includes one or more protuberances for extending into and interfitting with the apertures of the first body section to fit the first and second body sections together, for example, by way of a snap fitting, press fitting, heat staking, gluing, or other suitable mechanism. The one or more protuberances of the second body section may also fit through holes in a sling prior to interfitting into the one or more apertures of the first body section. Such holes include, without limitation, mesh openings or particularly created (and optionally reinforced) anchor engaging openings in the sling end. According to one feature, the sling includes holes along its length and the first and second body portions fit together through any of a plurality of the holes to adjust a functional length of the sling.

According to another configuration, the first body section includes a latch structure along an axially extending edge, the latch structure having an indent or through aperture, and the second body section includes a protuberance along a corresponding axial edge for snap fitting into the through aperture of the first body section to secure the first and second body sections together. An advantage to this configuration is that it enables a medical operator to easily remove the anchor from the sling if it needs to be moved to a different location along the sling. In this configuration, the body sections may also include the previously mentioned one or more apertures and protuberances for engaging with the sling openings, but they need not be sized and shaped for snap fitting together.

According to one embodiment, the body portion is elongated having a length that extends axially along the length of a sling (when attached) that is greater than a width that extends transversely across at least a portion of the width of the sling (when attached). According to an alternative embodiment, the body portion has a length and a width that are substantially equal. The body portion may have any suitable shape for attaching to the sling. By way of example, without limitation, it may be generally rectangular in nature, or alternatively may have rounded sides and be cylindrical in nature.

According to another embodiment, inner sling contacting surfaces of the first and second body sections may be ridged or otherwise textured to further engage with the sling to facilitate attachment to the sling end. According to a further embodiment, at least one of the first and second body sections include an axially extending slot/channel for slidably interfitting over a distal end of a shaft of a delivery device for implanting and positioning the anchor at an anatomical site.

According to another aspect, the fixation portion and the body portion of the tissue anchor are formed integrally with each other, and the anchor is separable into first and second sections, with each section including a body portion and a fixation portion. In one embodiment, the tissue anchor is elongated and is separable along a plane that extends axially through the tissue anchor. This aspect of the invention may include any of the features described above with respect to the separate body and fixation portion configuration.

In a further aspect, the invention is directed to a sling delivery system for delivering a sling assembly including a snap fit tissue anchor of the invention. According to one embodiment, the delivery system includes a shaft and a handle attached to a proximal end of the shaft. The shaft may be substantially straight or may include one or more curved sections. Additionally, the shaft may lie substantially in one plane or may be shaped to lie in multiple planes. The shaft may be of substantially constant outside diameter or may include portions of differing outside diameters. In various embodiments, the shaft may include hooked and/or helical portions.

According to one embodiment, the shaft includes a narrowed distal end for fitting into an axially extending slot/channel in the body of the tissue anchor. In one embodiment, the distal end of the shaft includes a shoulder extending radially outward. In one configuration, the shoulder extends around the entire circumference of the shaft. In other configurations, the shoulder extends around only a portion of the circumference. In both cases, the shoulder extends far enough to impede the tissue anchor from sliding proximally along the length of the shaft past the shoulder.

In a further embodiment, the sling delivery system includes a pusher assembly slidably interfitted over the shaft and slidably actuatable in a distal direction by a medical operator to push an end of a sling assembly off the distal end of the shaft. In one configuration of this embodiment, a distal end of the pusher assembly forms the shoulder, which contacts a proximal end of the body of the tissue anchor.

According to another aspect, the invention provides an implantable sling, either alone or as part of a sling delivery system. According to one configuration, the sling or a sling assembly including the sling includes features for indicating length measurements for aiding in positioning of the sling. According to one configuration, the sling and/or sling assembly also includes a feature for indicating a center location along the length of the sling, also for aiding in accurate sling placement. Preferably, the center feature, and the length measurement and/or position- indicating features are distinguishable from each other. By way of example, the length measurement and/or position-indicating features, and center features may be differently colored and/or of different widths.

In one configuration, protuberances of the tissue anchor extend through and engage with a double layer of sling material formed from folding the sling end lengthwise along the length indicating feature and toward the center indicating feature. In another configuration, the sling assembly includes preformed, structurally reinforced through apertures at its ends for engaging and interfitting the tissue anchor protuberances.

According to another aspect, the invention provides a method for delivering a sling to an anatomical location in a patient including the steps of snap fitting a tissue anchor onto a sling at a desired location, engaging a distal end of a delivery device with the tissue anchor, introducing the distal end of the delivery device with the tissue anchor so engaged into the body of the patient, and removing the distal end of the delivery device from the tissue anchor and the body of the. patient to deliver the sling to the anatomical location in the patient. According to one embodiment, the step of snap fitting includes snap fitting the tissue anchor onto the sling assembly at a length indicating feature. According to a further embodiment, the method includes the step of folding an end of a sling included in the sling assembly lengthwise at a length indicating feature to adjust the length of the sling, and the step of snap fitting includes snap fitting the tissue anchor over two layers of sling material near the length indicating feature. In another embodiment, the removing step includes actuating a pusher assembly to slide the tissue anchor off of the distal end of the delivery device.

According to a feature of the invention, the sling delivery systems and devices of the invention may be particularly sized and shaped for transvaginal/prepubic procedures. Such procedures, according to one approach, involve a single midline incision in the vaginal wall, through which both ends of the sling assembly are delivered. The tissue anchors at each end of the sling assembly may be positioned, for example, near or through an obturator membrane, in the periurethral tissues, in a prepubic space and/or in a retropubic space. According to another embodiment, the tissue anchors of the invention are formed from a biodegradable/bioabsorbable material. Preferably, the material is selected such that the tissue anchors dissolve at a rate that provides enough time for tissue to grow into the sling to hold the sling in place when the tissue anchors are gone.

Other aspects and advantages are described below.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 7A-7B are conceptual diagrams showing affixation of a sling end to an obturator membrane using a tissue anchor according to an illustrative embodiment of the invention.

FIGS. 8A-8B are conceptual diagrams showing affixation of a sling end to an obturator membrane using a tissue anchor according to an illustrative embodiment of the invention.

FIGS. 9A-9B are conceptual diagrams illustrating deficiencies in prior art sling assembly configurations.

DETAILED DESCRIPTION

Figure 1A:
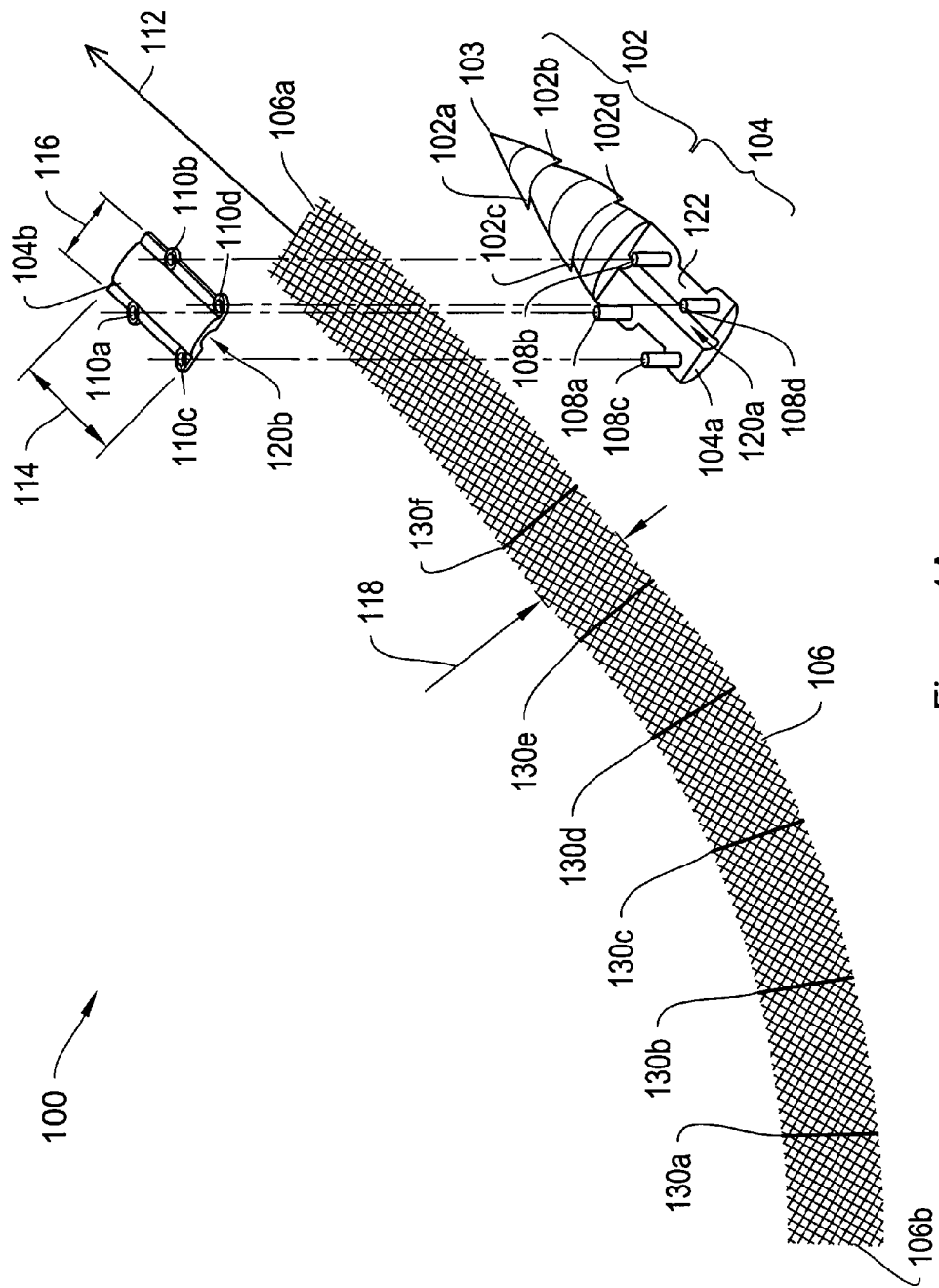
FIG. 1A is an exploded perspective view of a tissue anchor for affixing a sling end at an anatomical site according to an illustrative embodiment of the invention.

In general, the invention is directed to systems, methods and devices for treating urinary incontinence. As described below in more detail, in various illustrative embodiments, the invention provides systems, methods and devices employing an improved soft tissue anchor for anchoring a sling end in place, at least temporarily. According to one advantage, the tissue anchor of the invention facilitates delivery of a supportive sling to the periurethral tissue of a patient, without the need for abdominal or ishiopubic incisions. According to other advantages, the invention makes it easier for a medical operator to accurately place the supportive sling at a desired anatomical location. According to further advantages, the tissue anchor of the invention makes it easier for a medical operator to adjust the effective length of a sling, and also facilitates improved affixation of the sling ends to surrounding tissue.

Without limitation, examples of slings, sling assemblies, sling delivery devices and approaches, sling assembly-to-delivery device association mechanisms, and sling anchoring configurations with which the invention may be employed are disclosed in U.S. Pat. No. 6,042,534, entitled "Stabilization Sling for Use in Minimally Invasive Pelvic Surgery," U.S. Pat. No. 6,755,781, entitled "Medical Slings," U.S. Pat. No. 6,666,817, entitled "Expandable Surgical Implants and Methods of Using Them," U.S. Pat. No. 6,042,592, entitled "Thin Soft Tissue Surgical Support Mesh," U.S. Pat. No. 6,375,662, entitled "Thin Soft Tissue Surgical Support Mesh," U.S. Pat. No. 6,669,706, entitled "Thin Soft Tissue Surgical Support Mesh," U.S. Pat. No. 6,752,814, entitled "Devices For Minimally Invasive Pelvic Surgery," U.S. patent application Ser. No. 10/918,123, entitled "Surgical Slings," U.S. patent application Ser. No. 10/641,376, entitled "Spacer for Sling Delivery System," U.S. patent application Ser. No. 10/641,192, entitled "Medical Slings," U.S. patent application Ser. No. 10/641,170, entitled "Medical Slings," U.S. patent application Ser. No. 10/640,838, entitled "Medical Implant," U.S. patent application Ser. No. 10/460,112, entitled "Medical Slings," U.S. patent application Ser. No. 10/631,364, entitled "Bioabsorbable Casing for Surgical Sling Assembly," U.S. patent application Ser. No. 10/092,872, entitled "Medical 30 Slings," U.S. patent application Ser. No. 10/939,191, entitled "Devices for Minimally Invasive Pelvic Surgery," U.S. patent application Ser. No. 10/774,842, entitled "Devices for Minimally Invasive Pelvic Surgery," U.S. patent application Ser. No. 101774,826, entitled "Devices for Minimally Invasive Pelvic Surgery," U.S. patent application Ser. No. 10/015,114, entitled "Devices for Minimally Invasive Pelvic Surgery," U.S. patent application Ser. No. 10/973,010, entitled "Systems and Methods for Sling Delivery and Placement," U.S. patent application Ser. No. 10/957,926, entitled "Systems and Methods for Delivering a Medical Implant to an Anatomical Location in a Patient," U.S. patent application Ser. No. 10/939,191, entitled "Devices for Minimally Invasive Pelvic Surgery," U.S. patent application Ser. No. 10/918,123, entitled "Surgical Slings," U.S. patent application Ser. No. 10/832,653, entitled "Systems and Methods for Sling Delivery and Placement," U.S. patent application Ser. No. 10/642,397, entitled "Systems, Methods and Devices Relating to Delivery of Medical Implants," U.S. patent application Ser. No. 10/642,395, entitled "Systems, Methods and Devices Relating to Delivery of Medical Implants," U.S. patent application Ser. No. 10/642,365, entitled "Systems, Methods and Devices Relating to Delivery of Medical Implants," U.S. patent 15 application Ser. No. 10/641,487, entitled "Systems, Methods and Devices Relating to Delivery of Medical Implants," U.S. patent application Ser. No. 10/094,352, entitled "System for Implanting an Implant and Method, Thereof," U.S. patent application Ser. No. 10/093,498, entitled "System for Implanting an Implant and Method Thereof," U.S. patent application Ser. No. 10/093,450, entitled "System for Implanting an Implant and Method Thereof," U.S. patent application Ser. No. 10/093,424, entitled "System for Implanting an Implant and Method Thereof," U.S. patent application Ser. No. 10/093,398, entitled "System for Implanting an Implant and Method Thereof," and U.S. patent application Ser. No. 10/093,371, entitled "System for Implanting an Implant and Method Thereof," the entire contents of all of which are incorporated herein by reference.

FIG. 1A is an exploded perspective view of a tissue anchor 100 for affixing a sling end at an anatomical site according to an illustrative embodiment of the invention. As shown, the tissue anchor 100 includes a fixation portion 102 and a body portion 104. The fixation portion 102 may have any shape suitable for affixing the anchor within an anatomical membrane, muscle, ligament, soft tissue, bone or other anatomical site. By way of example, the fixation portion 102 may have edges, tapers, barbs or other protrusions for anchoring the fixation portion in place. According to the illustrative embodiment of FIG. 1A, the fixation portion 102 includes radially extending barbs 1 02a-I 02d. The barbs I 02a-I 02d are tapered to narrow toward a distal tip 103 of the anchor 100 to facilitate the anchor 100 passing into tissue and resist it being pulled out of the tissue.

The body portion 104 is sized and shaped to attach to a sling, such as the sling 106. According to the illustrative embodiment of FIG. 1A, the body portion 104 is separable into first 104a and second 104b sections, between which the sling 106 may be interfitted to attach the sling 106 to the tissue anchor 100. In the illustrative embodiment of FIG. 1A, the first 104a and second 104b body sections are two separate and distinct parts sized and shaped to fit 10 together. More particularly, one body portion, such as the first body portion 1 04a, includes one or more protuberances 1 08a-1 08d, and the other body portion, such as the second body portion 104b, includes one or more apertures 11 Oa-11 Od (which, optionally, may be through apertures) with which the protuberances 1 08a-108d interfit and engage to fit the first 104a and second 104b body portions together, for example, by way of a snap fitting, press fitting, heat staking, gluing, or other suitable mechanism. As shown, the protuberances 108a-108d of the second body section fit through holes in the mesh material of the sling 106 prior to interfitting into the apertures 110a-110d to secure the sling 106 between the first 104a and second 104b body sections. According to other illustrative embodiments, the holes in the sling 106 may include, without limitation, particularly created (and optionally reinforced) anchor engaging openings.

According to one feature, the sling 106 has an initial length as measured from one terminal end 106a to another terminal end 106b, and includes holes (such as the mesh openings) along its length. The first 104a and second 104b body portions may be fit together through any of the plurality of the holes along the length of the sling 106 to adjust a functional length of the sling, as measured between a first tissue anchor, such as the tissue anchor 100 and a second tissue anchor, not shown. The sling 106 may include markings, such as the transverse markings 130a-130f, for indicating length measurements of the sling. A marking, such as the marking 130d, may be included to indicate a middle location along the length of the sling 106. According to the depicted embodiment of FIG. 1A, the tissue anchor 100 is elongated in nature, with the tissue engaging portion 102 extending axially from the body portion 104. In 30 the illustrative embodiment of FIG. 1A, the tissue engaging portion 102 also extends substantially axially from the sling 106, as opposed to extending along an axis substantially offset from a sling axis 112. It should be noted that the sling axis 112 refers to an axis of the sling 106 taken along its length when it is extended in a substantially straight fashion.

The illustrative body portion 108 is also elongated and has a length 114 which extends axially along the length of the sling 106 (when attached) that is greater than a width 116 which extends transversely across at least a portion of the width 118 of the sling 106 (when attached). According to an alternative embodiment, the body portion 104 has a length 114 and a width 116 that are substantially equal. The body portion 104 may have any suitable shape for attaching to the sling 106. By way of example, without limitation, it may be generally rectangular in nature, or alternatively may have rounded sides and be cylindrical in nature.

According to the illustrative embodiment, inner sling contacting surfaces 122 of the first 104a and second 104b body sections may be ridged or otherwise textured to further engage with the sling 106 to facilitate attachment to the sling end. According to another feature, the first body section 104a includes an axially extending channel 120a and the second body section 104b includes an axially extending channel 120b. With the first 104a and second 104b body sections attached together, the first 120a and second 120b channels come together to form an enclosed axially extending channel 120 in the body portion 104. As described below in further detail with regard to FIGS. 3 and 4, the axially extending channel 120 is sized and shaped for interfitting over a distal end of a delivery device shaft. As also described below, in other illustrative embodiments, the channel 120 is sized and shaped for fitting over the finger of a medical operator.

Figure 1B:
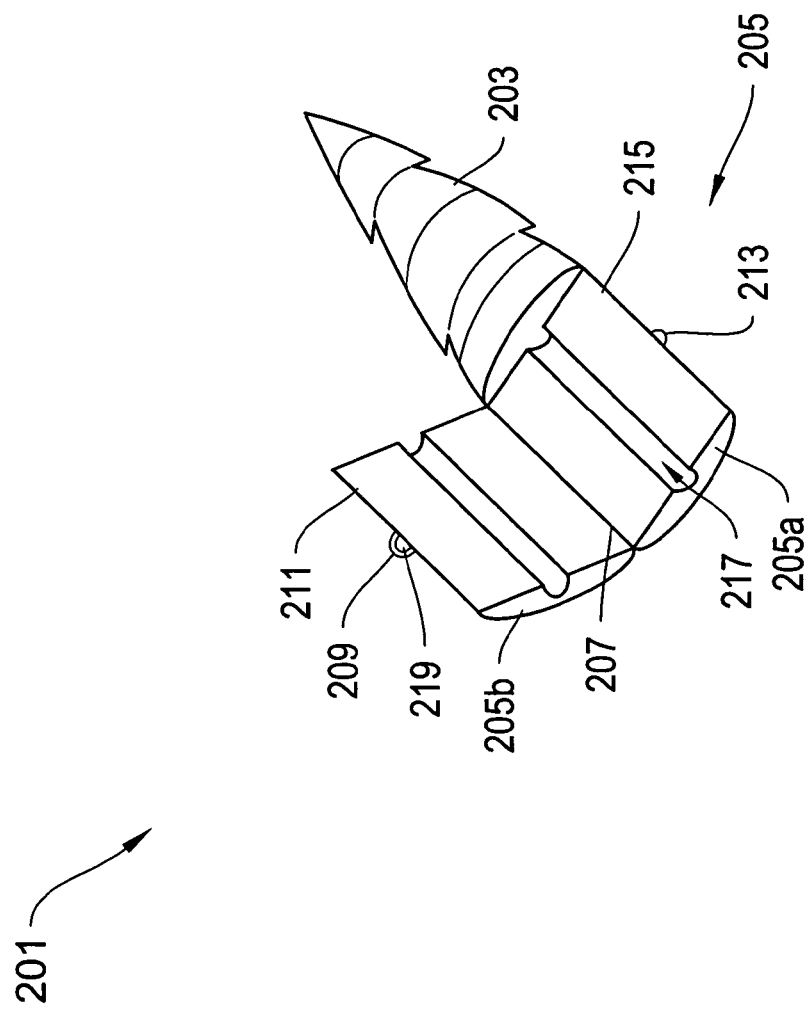
FIG. 1B is a front perspective view of a tissue anchor for affixing a sling end at an anatomical site according to an alternative illustrative embodiment of the invention.

FIG. 1B is a front perspective view of a soft tissue anchor 201 according to another illustrative embodiment of the invention. As in the case of the soft tissue anchor 100, the anchor 201 includes a tissue engaging portion 203 and a sling engaging body portion 205. Instead of 25 having two separable sections, such as the sections 104a and 104b, of FIG. 1A, the body portion 205 has two hinged sections 205a and 205b, hinged along an axially extending edge 207. According to the illustrative embodiment, the hinged sections 205a and 205b are integrally formed together, with the axially extending edge 207 being thinned sufficiently to enable hinge like motion between the two sections 205a and 205b. The hinged section 205b also includes a 30 latch 209 extending radially from an axially extending edge 211. The latch 209 includes an aperture 219 sized and shaped to snap fit with a protuberance 213 located along an axially extending edge 213. The body portion 205 also includes an axially extending channel 217 sized and shaped for interfitting over a distal end of a delivery device shaft. In a similar fashion to the embodiment of FIG. 1A, the two body sections 205a and 205b come together to sandwich and engage with a sling end there between.

Figure 2:
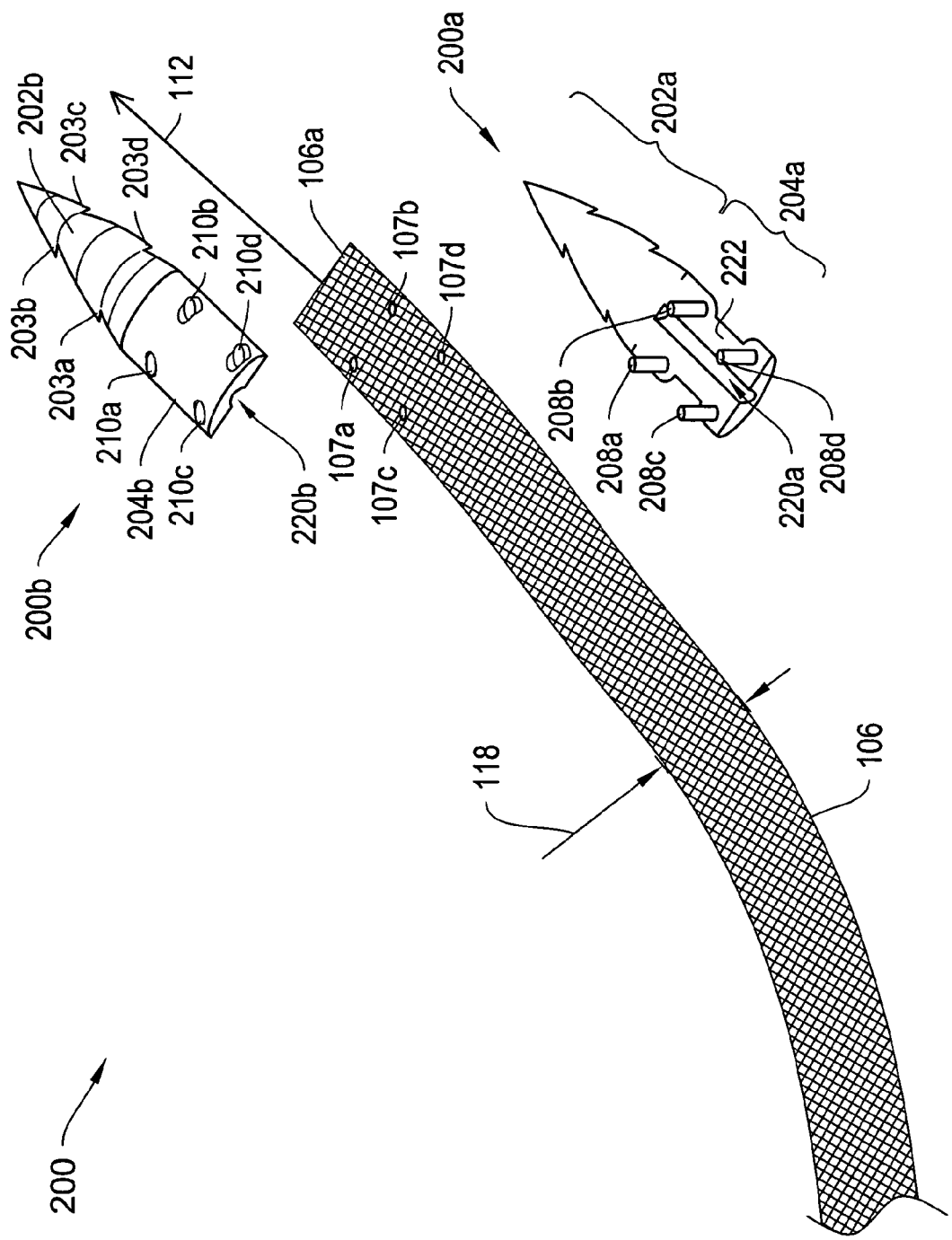
FIG. 2 is an exploded perspective view of a tissue anchor for affixing a sling end at an anatomical site according to another illustrative embodiment of the invention.

FIG. 2 is an exploded perspective view of a soft tissue anchor 200 for affixing an end 106a of a sling 106 at an anatomical site according to another illustrative embodiment of the invention. According to the illustrative embodiment of FIG. 2, the fixation portion 202 and the body portion 204 of the tissue anchor 200 are formed integrally with each other. The anchor 200 is separable into first 200a and second 200b sections. The first section 200a includes a fixation portion 202a and a body portion 204a. Similarly, the second section 200b includes a fixation portion 202b and a body portion 204b.

The fixation portions 202a and 202b come together to have any shape suitable for affixing the anchor 200 within an anatomical membrane, muscle, ligament, soft tissue, bone or other anatomical site. By way of example, the fixation portions 202a and 202b may have edges, tapers, barbs or other protrusions for anchoring the fixation portion in place. According to the illustrative embodiment of FIG. 2, the fixation portions 202a and 202b include radially extending barbs 203a-203d of the type depicted in FIG. 1A at 102a-102d.

The body portion 204 is sized and shaped to attach to a sling, such as the sling 106. According to the illustrative embodiment of FIG. 2, the first 204a and second 204b sections of the body portion 204 come together to sandwich and affix to the sling 106. In the illustrative embodiment of FIG. 2, the first 204a and second 204b body sections are two separate and distinct parts sized and shaped to fit together. More particularly, one body portion, such as the first body portion 204a, includes one or more protuberances 20S a-208d, and the other body portion, such as the second body portion 204b, includes one or more apertures 210a-210d (which, optionally, may be through apertures) with which the protuberances 20S a-20Sd interfit and engage to fit the first 200a and second 200b anchor portions together, for example, by way of a snap fitting, press fitting, heat staking, gluing, or other suitable mechanism. As shown, the protuberances 208a-208d of the second body section fit through reinforced holes 107a-107d in the mesh material of the sling 106 prior to interfitting into the apertures 210a-210d to secure the sling 106 between the first 204a and second 204b body sections.

As in the case of the illustrative embodiment of FIG. 1A, the tissue anchor 200 is elongated in nature, with the tissue engaging portion 202 extending axially from the body portion 204. The tissue engaging portion 202 also extends substantially axially from the sling 106, as opposed to extending along an axis substantially offset from a sling axis 112. The illustrative body portion 208 is also elongated and has a length which extends axially along the length of the sling 106 (when attached) that is greater than a width which extends transversely across at least a portion of the width 118 of the sling 106 (when attached). According to an alternative embodiment, the body portion 204 has a length and a width that are substantially equal. The body portion 204 may have any suitable shape for attaching to the sling 106. By way of example, without limitation, it may be generally rectangular in nature, or alternatively may have rounded sides and be cylindrical in nature.

As in the case of the illustrative embodiment of FIG. 1A, the inner sling contacting surfaces 222 of the first 204a and second 204b body sections may be ridged or otherwise textured to further engage with the sling 106 to facilitate attachment to the sling end 106a. According to another feature, the first anchor portion 200a includes an axially extending channel 220a and the second anchor portion 200b includes an axially extending channel 220b. With the first 200a and second 200b anchor portions attached together, the first 220a and second 220b channels come together to form an enclosed axially extending channel 220 in the anchor portion 200. As described below in further detail with regard to FIGS. 3 and 4, the axially extending channel 220 is sized and shaped for interfitting over a distal end of a delivery device shaft. As also described below, in other illustrative embodiments, the channel 220 is sized and shaped for fitting over the finger of a medical operator.

Although, FIGS. 1 and 2 depict the tissue anchors 100 and 200 as having separate and distinct body sections, 104a, 104b and 204a, 204b, respectively, this need not be the case. According to other illustrative configurations, one of the body sections, such as the first body section 104a/204a includes a latch structure along an axially extending edge. The latch structure may include, for example, an indent or through aperture. The other body section, such as the 30 second body section 104b/204b, includes a mating protuberance along a corresponding axial edge for snap fitting into the through aperture of the first body section to secure the first and second body sections together. An advantage to this configuration is that it enables a medical operator to easily remove the anchor 100/200 from the sling 106 if the anchor 100/200 needs to be moved to a different location along the sling 106. In this configuration, the body portions 104/204 may also include the previously mentioned one or more apertures and protuberances for engaging with the sling openings, but they need not be sized and shaped for snap fitting together, but instead only to secure the sling 106 in place between the body sections 104a, 104b or 204a, 204b.

In another illustrative embodiment, the sling 106 includes features for indicating length measurements for aiding in positioning of the anchors 100/200 along its length. According to one configuration, the sling also includes a feature for indicating a center location along its length. Preferably, the center feature, the length measurements, and the position-indicating features are distinguishable from each other. By way of example, the length measurement and/or position-indicating features, and center features may be differently colored and/or of different widths.

According to various illustrative embodiments, the tissue anchors 100 and 200 may be made of any suitable biocompatible material. The tissue anchors 100 and 200 may be made, for example, of a synthetic material such as nylon, polyethylene, polyester, polypropylene, fluoropolymers or a co-polymer thereof. In some illustrative embodiments, they may be formed, at least in part, from a mammalian tissue material such as bovine, porcine, equine, human cadaveric or engineered tissue. In some illustrative embodiments, the material of the anchors 100 and 200 may include a combination of synthetic and mammalian tissue materials.

According to other illustrative embodiments, at least a portion of the anchors 100 and 200 is biodegradable and may also dissolve and/or be absorbed into the patient's tissues. Exemplary biodegradable materials that may be employed for at least a portion of the anchors 100 and 200 include, but are not limited to, polylactic acid, polyglycolic acid and copolymers and mixtures thereof, such as poly(L-lactide) (PLLA), poly(D,L-lactide) (PLA), polyglycolic acid [polyglycolide (pGA)], poly(L-lactide-co-D,L-lactide) (pLLAlPLA), poly (L-lactide-coglycolide) (PLLAlPGA), poly(D,L-lactide-co-glycolide) (PLAlPGA), poly(glycolide-co-trimethylene carbonate) (PGNPTMC), poly(D,L-lactide-co-caprolactone) (PLNPCL), and poly(glycolide-co-caprolactone) (pGN-PCL); polyethylene oxide (PEO); polydioxanone (PDS); polypropylene fumarate; polydepsipeptides, poly(ethyl glutamate-co-glutamic acid), poly(tertbutyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

According to another feature, the anchors 100 and 200 may be configured to dissolve within a particular time range. The anchors 100 and 200 may be configured, for example, to substantially absorb (or have a portion that substantially absorbs) into the patient's tissues within about 2, 4, 6 or 8 or more weeks from the time the sling is implanted. Preferably, the anchors 15 100 and 200 remain structurally in tact long enough for scar tissue and/or other neighboring cells or tissues to grow into the sling 106 to effectively anchor it in place.

According to other illustrative embodiments, the sling 106 may be treated with one or more agents for release into the patient's tissues. One illustrative agent promotes, when applied to the patient's tissues in a pharmaceutically acceptable amount, well-organized collagenous tissue growth, such as scar tissue growth, preferably, in large quantities. According to one feature, the agent mayor may not block or delay the dissolvability of the sling 106. This may be controlled by selecting differing methods for loading the agent onto the sling 106. The tissue growth factor may include natural and/or recombinant proteins for stimulating a tissue response so that collagenous tissue, such as scar tissue, growth is enhanced. The tissue growth factor may similarly include natural and/or recombinant proteins for stimulating a tissue response so that non-scar tissue growth is enhanced. Furthermore, the tissue growth factor may include nonprotein, small molecule agents that mimic the effects of a natural and/or recombinant protein on scar or non-scar tissue growth. Exemplary growth factors that may be used include, but are not limited to, platelet-derived growth factor (pDGF), fibroblast growth factor (FGF), transforming growth factor-beta (TGF-beta), vascular endothelium growth factor (VEGF), ActivinlTGF and sex steroid, bone marrow growth factor, growth hormone, Insulin-like growth factor 1, and combinations thereof. Exemplary small molecule growth factors include, but are not limited to, small molecule agents that mimic the effects of one or more of the foregoing growth factors. The agent may also include a hormone, including but not limited to estrogen, steroid hormones, and other hormones to promote growth of appropriate collagenous tissue such as scar tissue. The agent may also include stem cells or other suitable cells derived from the host patient or derived from a suitable donor. Suitable cells include, without limitation, embryonic stem cells, adult stem cells, and other suitable non-stem cells. Stem or non-stem cells may be fibroblastic, mesenchymal, myoblastic, endothelial, and other cell types capable of maturing into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, genebased therapeutic agents, and combinations thereof. Such therapeutic agents include protein and non-protein, small molecule agents.

Exemplary steroidal anti-inflammatory therapeutic agents (glucocorticoids) include, but are not limited to, 21-acetoxyprefuenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, .fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof. Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromo saligenin, calcium acetylsalicylate, diflunisal, etersalate, fendosal, gentisic acid, glycol salicylate, imidazole salicylate, lysine acetylsalicylate, mesalamine, morpho line salicylate, I-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as € -acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromo salicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-Iactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-Itrimethyl, 3-diphenyl-propylamine, tropenzile, trospium chloride, xenytropium bromide, and pharmaceutically acceptable salts thereof.

As mentioned above with regard to FIGS. 1 and 2, the soft tissue anchors of the invention may be employed with any suitable delivery device, or with no delivery device at all.

Figure 3:
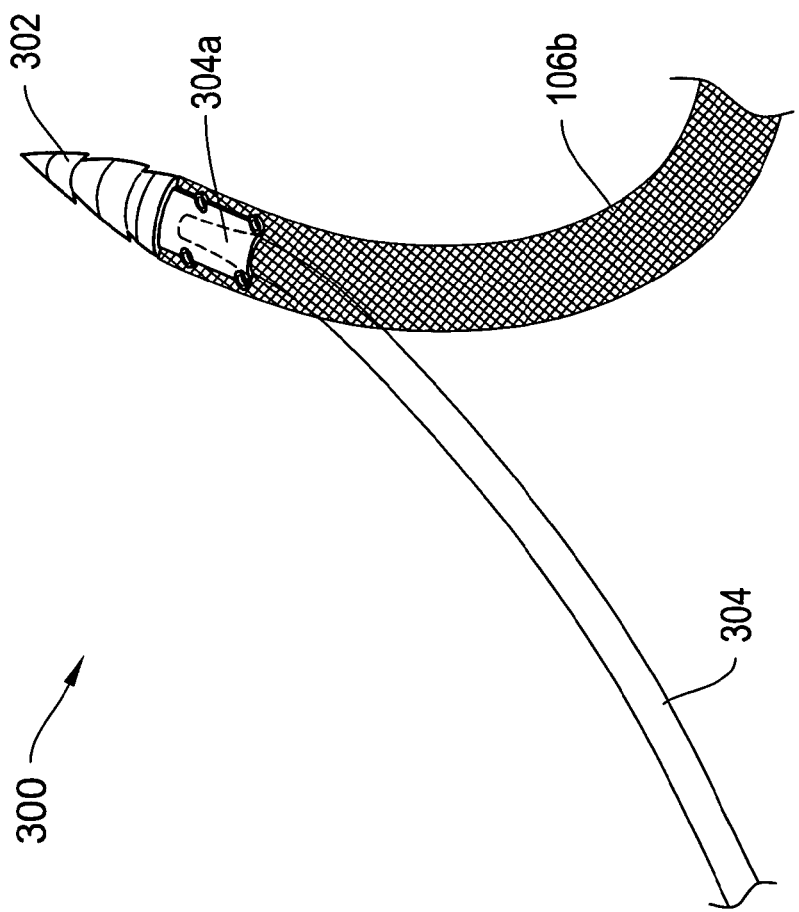
FIG. 3 shows a sling assembly of the invention interfitted over a distal end of a shaft of a delivery device.

FIG. 3 shows a portion of a system 300 for implanting a sling 106 at an anatomical location in the body of a patient according to an illustrative embodiment of the invention. The system 300 includes a sling 106 having a soft tissue anchor 302 of the type described above with respect to FIGS. 1 and 2 affixed to one of its ends. The system 300 also includes a delivery device shaft 304 having a distal end 304a interfitted into an anchor channel, such as the anchor channels 120 and 220 described with respect to FIGS. 1 and 2, respectively, above. The shaft 304 may be substantially straight, curved or include both curved and straight portions. The distal tip of the shaft 304 is illustratively conically shaped. However, any suitable tip shape may be employed.

Figure 4:
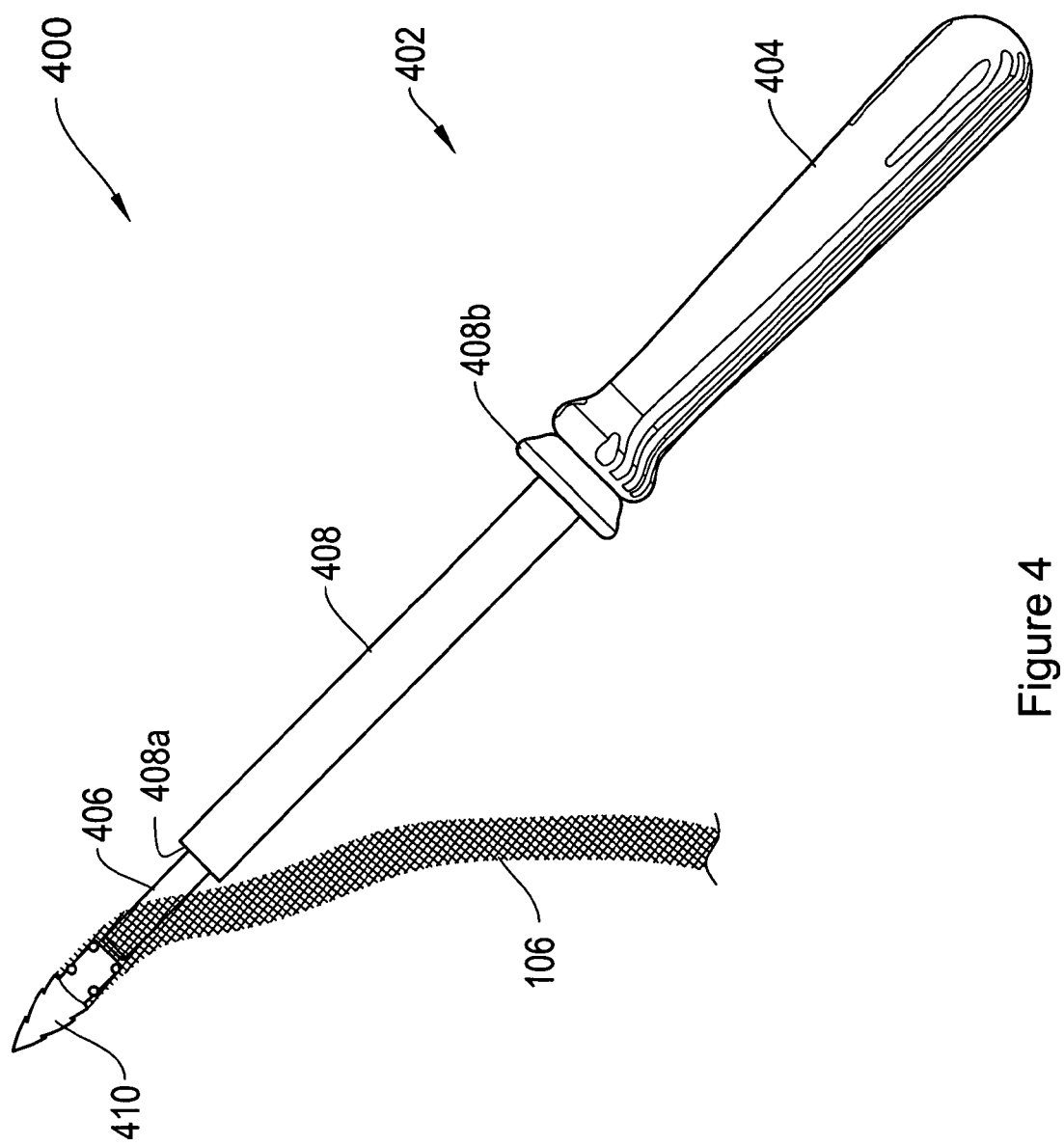
FIG. 4 shows a sling assembly of the invention interfitted over a distal end of a delivery device employing a pusher assembly according to an illustrative embodiment of the invention.

FIG. 4 shows a system 400 for implanting a sling 106 at an anatomical location in the body of a patient according to another illustrative embodiment of the invention. The sling 106 and anchor 410 are substantially the same as the anchors and sling of FIGS. 1-3. The delivery device 402 includes a handle 404 and a shaft 406 extending distally from the distal end of the handle 404. As in the case of the shaft 304, the shaft 404 may be substantially straight, curved or include both curved and straight portions. A pusher assembly 408 slidably interfits over the shaft 406. The pusher assembly 408 includes a shoulder 408a and an actuator 408b. A medical operator slides the pusher assembly 408 distally along the shaft 406 using the actuator 408b. The shoulder 408a abuts a proximal end of the anchor 410 to slide the anchor 410 distally off the distal end of the shaft 406 to place the anchor 410 at a desired location in the soft tissue of a patient.

Figure 5:
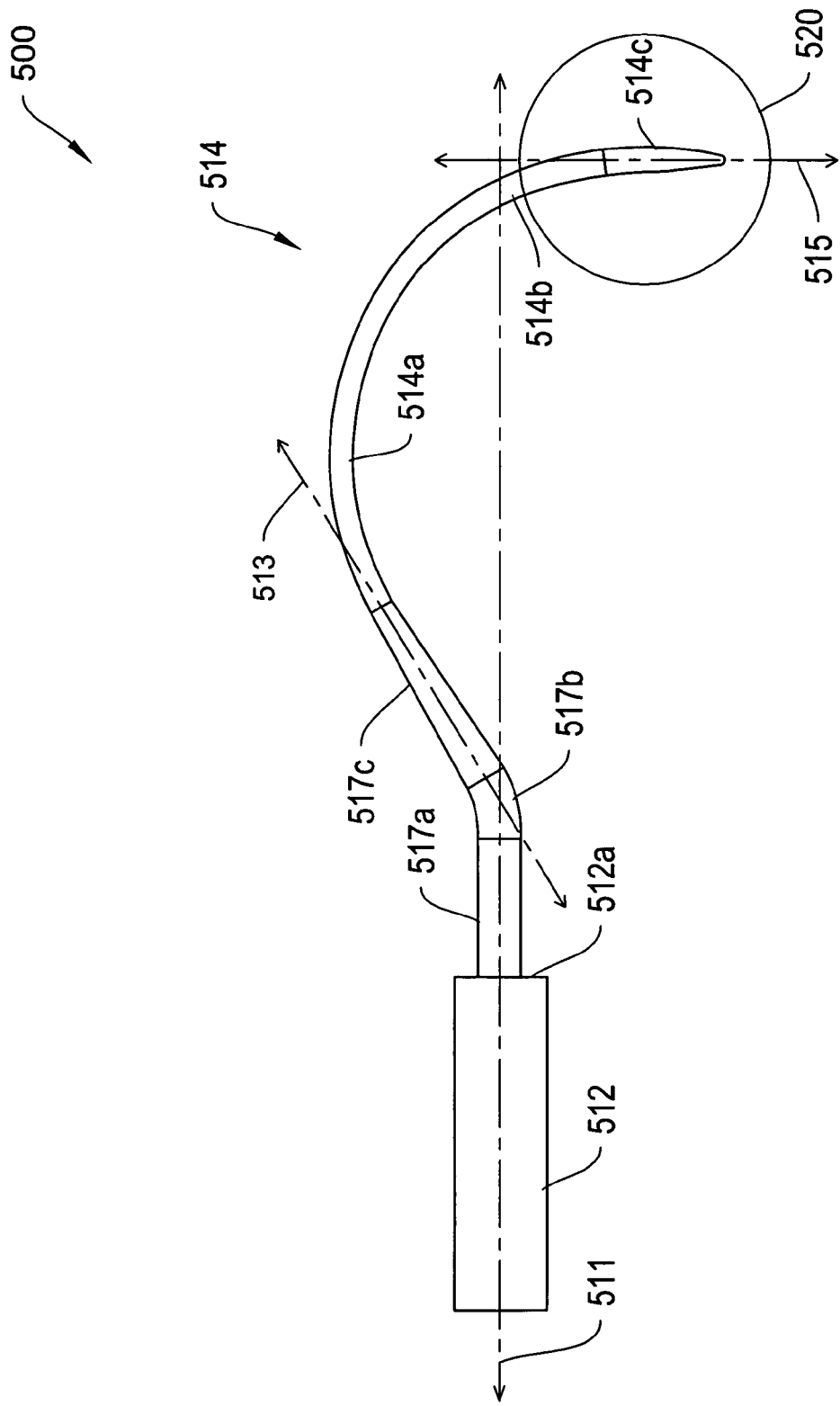
FIG. 5 shows a delivery device according to an illustrative embodiment of the invention.

FIG. 5 shows another illustrative delivery device particularly sized and shaped for transobtural placement of an implantable sling 106 employing a soft tissue anchor, such as the anchors 100,200,302, and 410 described above. FIG. 5 depicts a side view of the delivery device 500 according to an illustrative embodiment of the invention. The delivery device 500 includes a handle 512, a shaft 514, and a transitional portion 517 extending distally between a distal end 512a of the handle 512 and a proximal end of the shaft 514. The transitional portion 517 includes a first straight section 517a, a curved section 517b and a second straight section 517c, all lying substantially in a single plane, and may be formed as either part of the shaft 514 or as part of the handle 512. The shaft 514 includes a curved section 514a, a straight section 514b and a conical tip 514c, all lying substantially in the same plane as the transitional portion 517. In the illustrative embodiment, the first straight section 517a of the transitional portion 617 attaches to the distal end 512a of the handle 512, extends distally along a first axis 511, and preferably has a substantially constant diameter. The curved section 517b of the transitional portion 517 extends from a distal end of the first straight section 517a, curves away from the first axis 511, and also preferably has a substantially constant diameter. The second straight section 517c extends from a distal end of the curved section 517b along a second axis 513, and preferably has a diameter that decreases from its proximal end to its distal end to provide increased structural stability to the shaft 514. The curved section 514a, preferably, has a substantially constant diameter, smaller than the diameter of the curved section 517b of the transitional portion 517, and extends from the distal end of the second straight section 517c of the transitional portion 517, curves back toward the first axis 511, and terminates at a distal end approximately at an intersection with the first axis 511. The straight section 514b, preferably, has a substantially constant diameter and extends from the distal end of the curved section 514a along a third axis 515, which crosses the first axis 511. In one configuration, a conical tip 514c extends distally from the straight section 514b. In another configuration, the distal end 519 of the delivery device 510 may include a structure or feature for associating the delivery device 510 with a sling and/or sling assembly or an end of a sling and/or sling assembly. A distal portion 520 of the delivery device 510 may include, for example, a structure or feature, such as a tapered distal portion as depicted in FIG. 5, or a shoulder as depicted at 408a in FIG. 4, for abutting a proximal end of a soft tissue anchor.

Figure 6C:
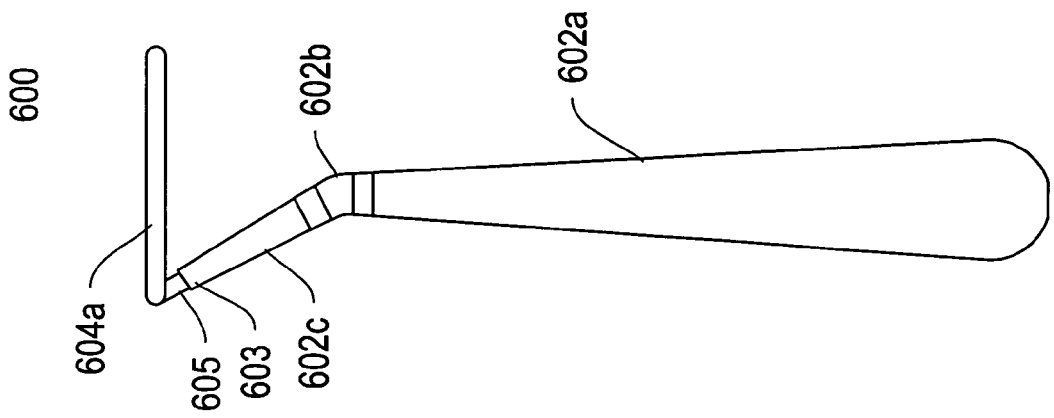
FIGS. 6A-6C show delivery devices according to illustrative embodiments of the invention.
Figure 6B:
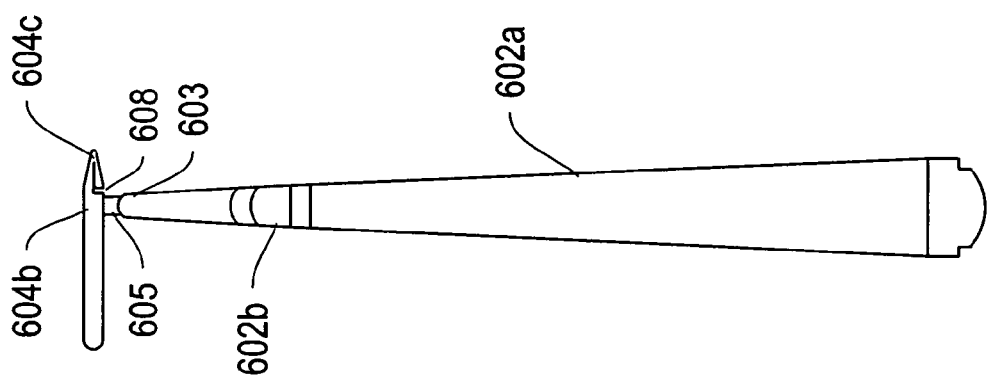
Figure 6A:
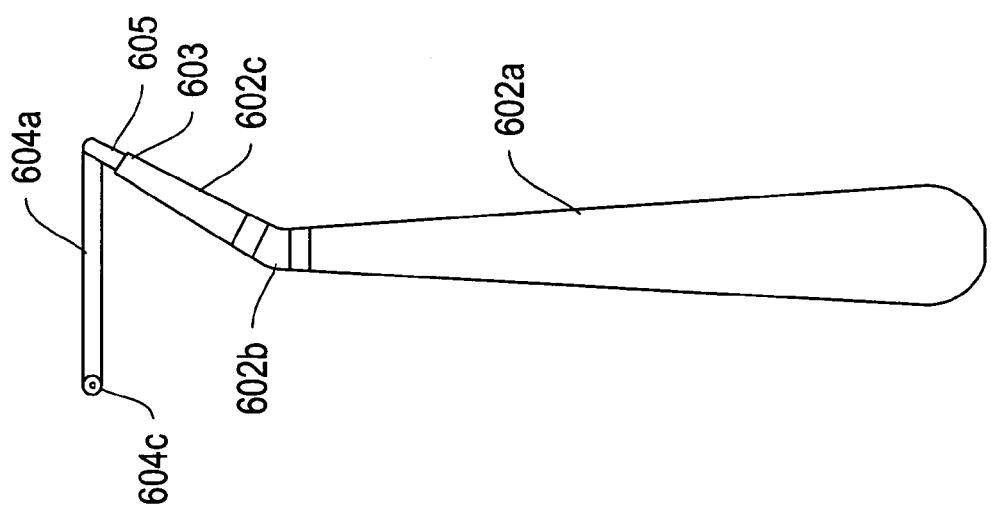

FIGS. 6A-6C show another illustrative delivery devices 600 also particularly sized and shaped for transobtural placement of an implantable sling, and employable with any of the illustrative embodiments of FIGS. 1-4. The delivery devices 600 includes a handle 602 with first 602a and second 602b substantially straight sections located substantially in a first plane and angled relative to each other, a transitional portion 605 extending out of a distal end 603 of the handle 602, and a shaft 604 extending from a distal end of the transitional portion 605. The shaft includes curved section 604a, a straight section 604b, and in one configuration, terminates in a conical tip 604c. In another configuration, the distal end 609 of the delivery device 600 may include a structure or feature for associating the delivery device 600 with a sling and/or sling assembly or an end of a sling and/or sling assembly. A distal portion 600 of the delivery device 600 may include, for example, a structure or feature, such as a tapered distal portion as depicted in FIG. 5, or a shoulder as depicted in FIG. 4, for abutting a proximal end of a soft tissue anchor.

The transitional portion 605 interfits and extends axially out of the distal end 603 of the second handle section 602c to affix the shaft 604 to the handle 602. As a result, the transitional portion 605 is substantially co-planer with the handle 602 in the first plane. The curved section 604a of the shaft 604 extends from a distal end of the transitional portion 605. The straight section 604b of the shaft 604 extends from a distal end of the curved section 604a. The curved section 604a and the straight section 604b are substantially coplanar in a second plane. According to the illustrative embodiment of FIGS. 6A-6C, the first and second planes are substantially orthogonal to each other. However, the first and second planes may be at any suitable angle (e.g., about 10, 20, 30, 45, 60, 70 or 80 degrees) to each other.

To provide structural reinforcement, sections 602b and 602c have a cross sectional diameter that tapers to be smaller at the distal end 603 of the handle 602. Additionally, rather than having the tapered section 607c of the transitional portion 607 being formed as part of the shaft 604, as shown in FIG. 5, the tapered portions 602b and 602c of the embodiment of FIGS. 6A-6C are formed as part of the handle 602. According to one feature, this configuration reduces the length of the transitional portion 605 and thus, provides improved structural support for the curved section 604a. Preferably, in operation, neither the handle 602 nor the intermediate/transitional portion 605 extends into the body of the patient, and provides a positive stop against this occurring.

According to other illustrative features, the invention is directed to various methods of implanting a sling 106 including a soft tissue anchor 100 at an anatomical location in the body of a patient. According to some methods, the sling is implanted via an initial transvaginal incision, and avoids the need for any abdominal or ishiopubic incisions.

Figure 7B:
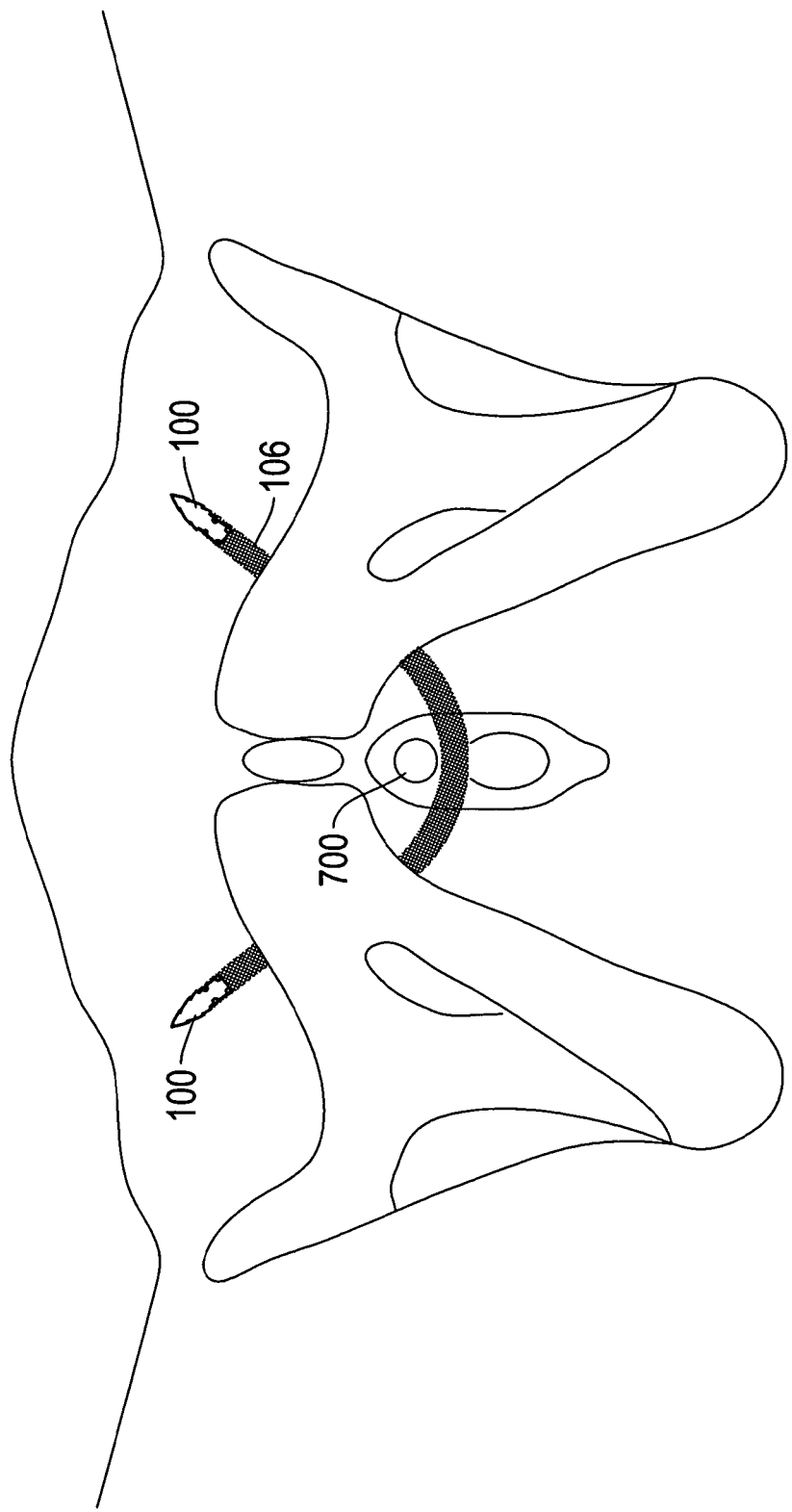

FIGS. 7 A and 7B depict one illustrative method of implanting the sling 106 in the periurethral tissue of a patient to form a platform under the urethra 700. As shown in FIG. 7 A, an incision 702 is made in the anterior vaginal wall and dissected bilaterally to the interior portion of the inferior pubic ramus. The soft tissue anchor 100 attached to an end of a sling 106 is interfitted over the distal end of a delivery device shaft 704. A medical operator grasps the delivery device handle 706 and passes the shaft 704 with the anchor 100 installed through the vaginal incision and upward into a desired anchoring location on a first side of the urethra 700, preferably, without piercing the abdomen. The anchoring location may be in any suitable abdominal soft tissue, such as without limitation, the retropubic space between the bladder and the abdomen, the space of Retzius, the Cooper's ligament. Additionally, the anchoring location may be in front of or behind the pubic bone. Once the anchor 100 is placed at the desired location, the delivery device shaft 704 is withdrawn leaving the anchor 100 in place. As shown in FIG. 7B, the procedure is repeated on the contralateral side of the body, with the same or a second delivery device, to place the sling 106 under the urethra.

Figure 8B:
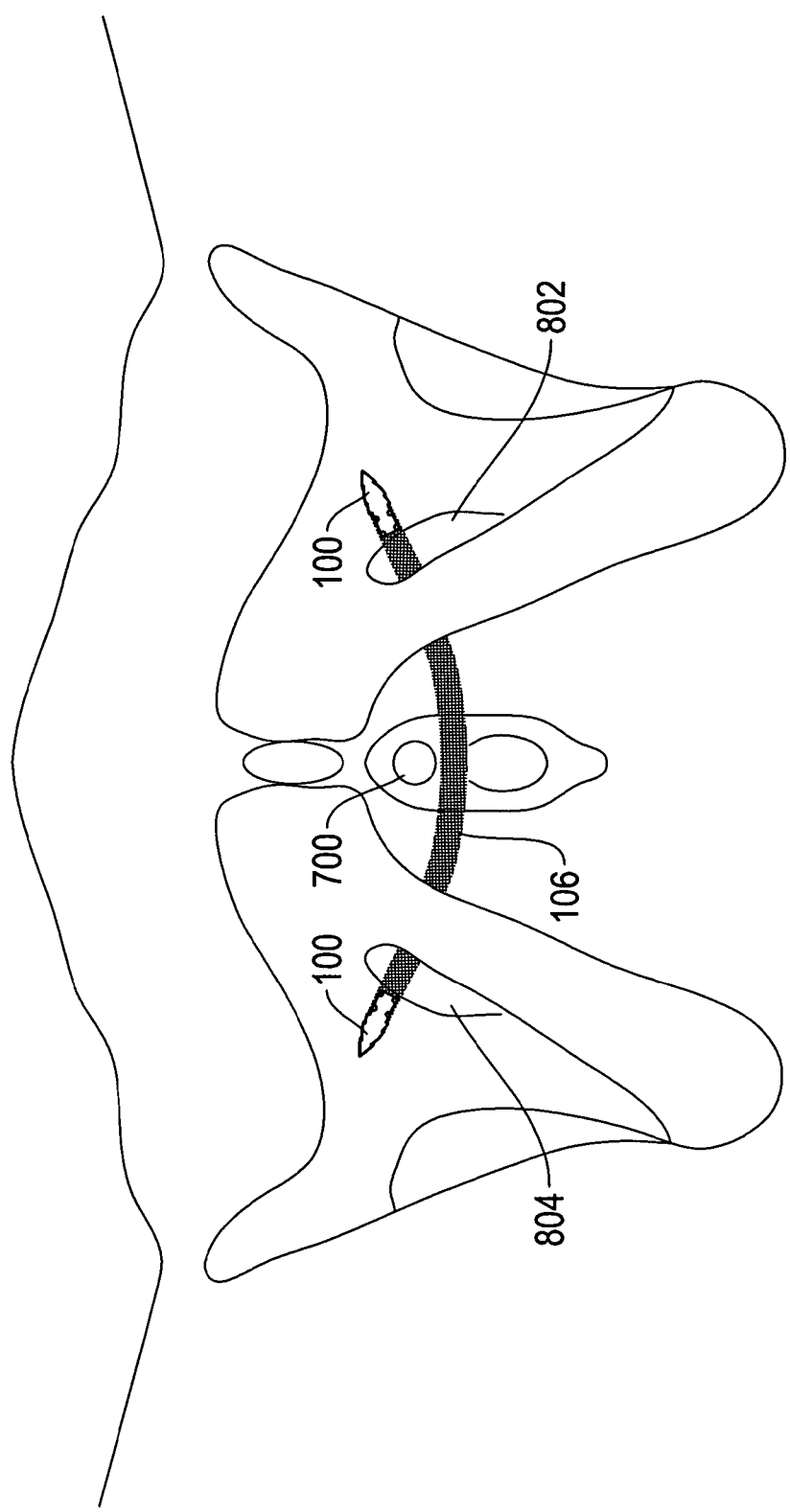

FIGS. 8A and 8B depict another illustrative embodiment in which the invention employs a delivery device such as depicted in FIG. 5 or 6A-6C to position at least one of the first 106a and second 106b ends of the sling 106 near or through an obturator foramen (i.e., transobturally) and/or obturator membrane. The delivery device 500 is employed to describe this embodiment. However, the delivery device 600 may be employed in a similar fashion. As shown in FIG. 8A, an incision 702 is once again made in the anterior vaginal wall and dissected bilaterally to the interior portion of the inferior pubic ramus. The soft tissue anchor 100 attached to an end of the a sling 106 is interfitted over the distal end of the delivery device shaft 514. A medical operator grasps the handle 512 and inserts the delivery device shaft 514 with the anchor 100 installed through the vaginal incision 702 in a lateral motion passing behind the ishiopubic ramus and piercing the obturator membrane 802. As shown in FIG. 8A, the delivery device shaft 514 can then be withdrawn from the body leaving the anchor 100 implanted in or through the obturator membrane 802. This process is repeated with the same or a second delivery device and the second soft tissue anchor on the contralateral side of the body.

One advantage is that it enables an operator to accurately place a sling end with a soft tissue anchor attached. Another advantage is that the anchor and sling configuration facilitate placement of a sling end through the obturator membrane. FIGS. 9A and 9B depict one drawback of prior art anchoring approaches. As shown, according to some prior art approaches, the anchor 900 extended axially from a sling end, such as the sling end 902a of the sling 902, but did not also extend axially toward an opposite sling end. Consequently, if the anchor 900 were implanted within the obturator membrane 802 and a dissolvable anchor were employed subsequent to the anchor 900 dissolving, the sling end 902a would no longer be anchored in the obturator membrane 802. Thus, anchor configurations are not suitable for bioabsorbable applications where the sling end is to be anchored in the obturator membrane.

Figure 10B:
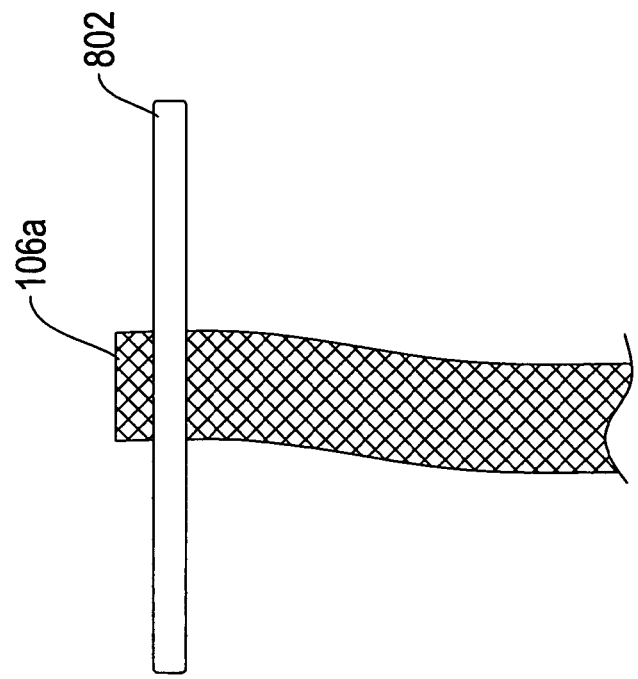
FIGS. 10A-10B show a tissue anchor for affixing a sling end at an anatomical site according to an illustrative embodiment of the invention.
Figure 10A:
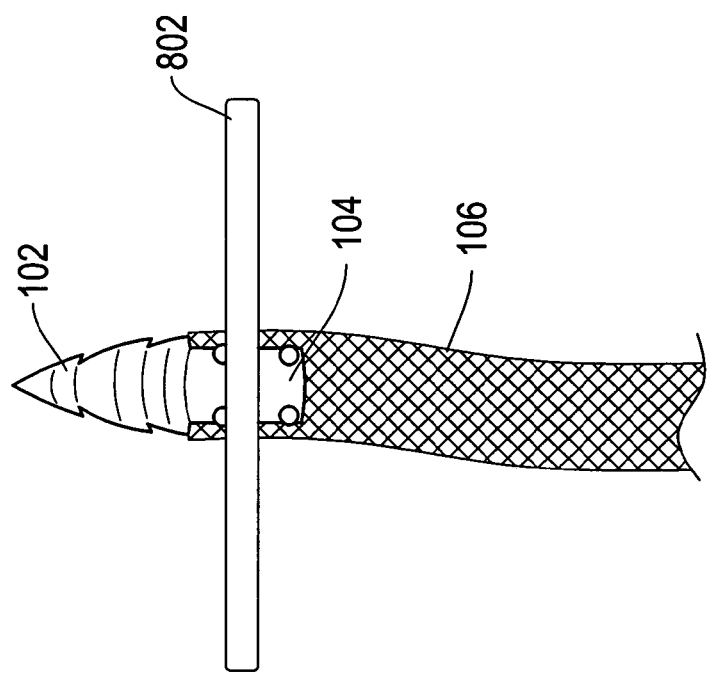

In contrast to the deficiencies of the embodiment of FIGS. 9A and 9B, the soft tissue anchor 100 of the invention is particularly suited for anchoring in the obturator membrane, even when formed from a bioabsorbable material. More specifically, as shown in FIGS. 10A and 10B, the affixation portion 102 of the soft tissue anchor 100 extends axially from the sling end 106a while the body portion 104 extends axially along the sling toward the opposite sling end 106b. With this configuration, the sling end 106a is positioned through the obturator membrane 802. Thus, when the anchor 100 dissolves, the sling end 106a remains securely anchored in through obturator membrane 802.

Another advantage of the above described invention is that it enables a medical operator to place a supportive sling under the bladder neck or the mid-urethra to provide a urethral platform, without requiring any incision other than those made in a vaginal wall. More particularly, employing the devices, systems, methods and features of the invention, a medical operator can place an implantable sling without making any abdominal or ishiopubic incisions.

It should be understood that for the described procedures, and other procedures using the described devices and systems, the delivery devices and sling and/or sling assembly may be tailored, for example, in the dimensions of the devices, such as length, diameter, shape, and curvature; sling assembly, such as length and width of the sling or suture thread; and for a particular method of delivery or for placement to a specific anatomical site.

What is claimed is:

1. A tissue anchor, comprising:
a tissue engaging portion configured to engage bodily tissue to help retain the tissue anchor within a body of a patient; and
a receiving portion having a sidewall defining a channel, the channel having a closed end portion and being configured to receive a portion of a sling and a portion of a delivery device such that the portion of the sling is disposed between the portion of the delivery device and the sidewall, the receiving portion including a first section and a second section, the first section including a plurality of apertures at least partially disposed through an inner contacting surface of the first section such that the first section fully surrounds each aperture, the second section including a plurality of protuberances extending from an inner contacting surface of the second section, the plurality of protuberances configured to pass through the sling and matingly interfit with the plurality of apertures of the first section.

2. The tissue anchor of claim 1, wherein the apertures are holes extending entirely through the first section.

3. The tissue anchor of claim 1, wherein the apertures and the protuberances are sized and shaped for snap fitting together.

4. The tissue anchor of claim 1, wherein the apertures and the protuberances are sized and shaped for reversibly and reusably interfitting together.

5. The tissue anchor of claim 1, wherein at least one of the tissue engaging portion and the receiving portion are formed at least in part from a bioabsorbable material.

6. A system for implanting a sling into a body of a patient, comprising:
a sling configured to be placed in the body of a patient;
a tissue anchor having a tissue engaging portion configured to engage bodily tissue to help retain the sling within the body of the patient, and a receiving portion having a sidewall defining a channel having a closed end, the receiving portion including a first section and a second section, the first section including a plurality of apertures at least partially disposed through an inner contacting surface of the first section such that the first section fully surrounds each aperture, the second section including a plurality of protuberances extending from an inner contacting surface of the second section, the plurality of protuberances configured to pass through the sling and matingly interfit with the plurality of apertures of the first section, the tissue anchor coupled to the sling, a portion of the sling being disposed in the channel, a portion of the sling being disposed between the first section and the second section; and a delivery device including a shaft, the channel being configured to receive a portion of the shaft of the delivery device such that the portion of the sling disposed in the channel is disposed between the portion of the shaft of the delivery device and the sidewall.

7. The system of claim 6, wherein the delivery device includes a pusher slidably coupled to the shaft and configured to move from a first position to a second position different than the first position to disengage the tissue anchor from the shaft.

8. The system of claim 6, wherein the apertures are through apertures.

9. The system of claim 6, wherein the apertures and the protuberances are sized and shaped for snap fitting together.

10. The system of claim 6, wherein the apertures and the protuberances are sized and shaped for reversibly and reusably interfitting together.

11. A method for implanting a sling in the periurethral tissues of a body of a patient, the method comprising, coupling a sling to a tissue anchor, the tissue anchor including a tissue engaging portion configured to engage bodily tissue to retain the sling within the body, the tissue anchor also including a receiving portion having a sidewall defining a channel, the receiving portion including a first portion and a second portion, wherein the coupling includes coupling the second portion with the first portion such that a portion of the sling is disposed within the channel between the first section and the second section;

interfitting the receiving portion of the tissue anchor over a distal end of a sling delivery device shaft such that a portion of the distal end of the sling delivery device shaft is disposed within the channel defined by the sidewall of the tissue anchor, the portion of the sling being disposed between the portion of the distal end of the sling delivery device shaft and the sidewall, and inserting the distal end of the sling delivery device shaft with the tissue anchor interfitted into the body of the patient to implant the sling in the periurethral tissues of the patient.

12. The method of claim 11, wherein the inserting includes inserting the distal end of the sling delivery device shaft and the tissue anchor into the body of the patient via an incision in a vaginal wall of the patient.

13. The method of claim 11, further comprising:
delivering the tissue anchor to the space of Retzius.

14. The method of claim 11, further comprising:
delivering the tissue anchor at least partially through a first obturator membrane.

15. The method of claim 11, wherein the tissue anchor is a first tissue anchor, the method further comprising, interfitting a receiving portion of a second anchor over the distal end of the sling delivery device shaft, and inserting the distal end of the sling delivery device shaft with the second tissue anchor interfitted into the body of the patient to implant the sling in the periurethral tissues of the patient.

16. The method of claim 15, further comprising:
inserting the distal end of the sling delivery device shaft and the second tissue anchor into the body of the patient via an incision in a vaginal wall of the patient.

17. The method of claim 16, further comprising:
delivering the second tissue anchor to the space of Retzius.

* * * * *